United States Patent
Addington et al.

(10) Patent No.: US 8,573,203 B2
(45) Date of Patent: *Nov. 5, 2013

(54) NEBULIZER HAVING FLOW METER FUNCTION

(75) Inventors: W. Robert Addington, Melbourne Beach, FL (US); Stuart P. Miller, Indialantic, FL (US); Michael M. Phelipa, Melbourne, FL (US); Robert E. Stephens, Parkville, MO (US)

(73) Assignee: Pneumoflex Systems, LLC, Melbourne, FL (US)

( * ) Notice: Subject to any disclaimer, the term of this patent is extended or adjusted under 35 U.S.C. 154(b) by 77 days.

This patent is subject to a terminal disclaimer.

(21) Appl. No.: 13/293,633

(22) Filed: Nov. 10, 2011

(65) Prior Publication Data
US 2012/0053482 A1    Mar. 1, 2012

Related U.S. Application Data

(63) Continuation of application No. 12/724,785, filed on Mar. 16, 2010, now Pat. No. 8,109,266, and a continuation-in-part of application No. 11/557,993, filed on Nov. 9, 2006, now Pat. No. 7,726,306, which is a continuation-in-part of application No. 11/431,689, filed on May 10, 2006, now Pat. No. 7,712,466, which is a continuation-in-part of application No. 10/783,442, filed on Feb. 20, 2004, now abandoned.

(60) Provisional application No. 61/160,735, filed on Mar. 17, 2009.

(51) Int. Cl.
A61M 15/00    (2006.01)

(52) U.S. Cl.
USPC ....................................... 128/203.12

(58) Field of Classification Search
USPC ....................................... 128/203.12
See application file for complete search history.

(56) References Cited

U.S. PATENT DOCUMENTS 2,280,050 A    4/1942    Alexander et al. ....... 128/203.11
3,097,645 A    7/1963    Lester ......................... 128/194

(Continued)

FOREIGN PATENT DOCUMENTS

EP    0667168    2/1994

OTHER PUBLICATIONS

Joseph L. Rau, "2004 Philip Kittredge Memorial Lecture, *The Inhalation of Drugs: Advantages and Problems*," Respiratory Care, Mar. 2005, vol. 50, No. 3, pp. 367-382.

(Continued)

*Primary Examiner* — Nicholas Lucchesi
*Assistant Examiner* — Diva K Chander
(74) *Attorney, Agent, or Firm* — Allen, Dyer, Doppelt, Milbrath & Gilchrist, P.A.

(57) ABSTRACT

In accordance with non-limiting examples, a nebulizer includes a main body comprising an air channel section and further comprising a mixing chamber and a venturi positioned to be placed within the patient's oral cavity and configured to receive medicine and air and mix the medicine and air within the mixing chamber and receive the air flow through the venturi and cause the medicine entering the mixing chamber to be atomized by the action of air flowing through the venturi. An air flow sensor is associated with the main body and configured to measure the air flow created by the patient's one of at least inhaling and exhaling air.

10 Claims, 26 Drawing Sheets

MEDICINE FEED LINE ENTERS MIXING CHAMBER

(56) References Cited

U.S. PATENT DOCUMENTS

| | | | | |
|---|---|---|---|---|
| 3,998,226 | A | 12/1976 | Harris | 128/203.15 |
| 4,253,468 | A | 3/1981 | Lehmbeck | 128/726 |
| 4,333,450 | A | 6/1982 | Lester | 128/200.14 |
| 4,792,097 | A | 12/1988 | Kremer, Jr. et al. | 239/338 |
| 4,852,582 | A | 8/1989 | Pell | 128/716 |
| 4,884,460 | A * | 12/1989 | Nowacki et al. | 73/861.52 |
| RE33,717 | E | 10/1991 | Svoboda | 239/338 |
| 5,312,046 | A | 5/1994 | Knoch et al. | 239/338 |
| 5,363,842 | A * | 11/1994 | Mishelevich et al. | 128/200.14 |
| 5,411,208 | A | 5/1995 | Burgener | 239/8 |
| 5,598,838 | A | 2/1997 | Servidio et al. | 128/204.23 |
| 5,676,132 | A * | 10/1997 | Tillotson et al. | 128/204.23 |
| 5,678,563 | A | 10/1997 | Addington et al. | 128/716 |
| 5,685,291 | A | 11/1997 | Marsh | 128/200.15 |
| 5,823,187 | A | 10/1998 | Estes et al. | 128/204.23 |
| 5,839,430 | A * | 11/1998 | Cama | 128/200.14 |
| 6,004,268 | A | 12/1999 | Addington et al. | 600/300 |
| 6,029,660 | A | 2/2000 | Calluaud et al. | 128/203.12 |
| 6,044,841 | A | 4/2000 | Verdun et al. | 128/200.18 |
| 6,050,953 | A | 4/2000 | Warwick et al. | 600/538 |
| 6,085,741 | A | 7/2000 | Becker | 128/200.21 |
| 6,183,423 | B1 * | 2/2001 | Gaumond et al. | 600/529 |
| 6,223,745 | B1 | 5/2001 | Hammarlund et al. | 128/200.18 |
| 6,267,006 | B1 * | 7/2001 | Bugli et al. | 73/114.34 |
| 6,398,728 | B1 | 6/2002 | Bardy | 600/300 |
| 6,411,843 | B1 | 6/2002 | Zarychta | 600/546 |
| 6,435,183 | B1 * | 8/2002 | Farman | 128/204.25 |
| 6,568,387 | B2 | 5/2003 | Davenport et al. | 128/200.24 |
| 6,655,376 | B2 | 12/2003 | Addington et al. | 128/200.24 |
| 6,679,250 | B2 | 1/2004 | Walker et al. | 128/200.21 |
| 6,698,422 | B2 | 3/2004 | Fugelsang et al. | 128/200.14 |
| 6,729,327 | B2 * | 5/2004 | McFarland, Jr. | 128/203.12 |
| 6,735,471 | B2 | 5/2004 | Hill et al. | 607/2 |
| 6,848,443 | B2 | 2/2005 | Schmidt et al. | 128/200.23 |
| 7,013,894 | B2 * | 3/2006 | McFarland, Jr. | 128/205.24 |
| 7,191,780 | B2 * | 3/2007 | Faram | 128/204.25 |
| 7,198,044 | B2 * | 4/2007 | Trueba | 128/200.16 |
| 7,270,123 | B2 | 9/2007 | Grychowski et al. | 128/200.14 |
| 7,712,466 | B2 * | 5/2010 | Addington et al. | 128/200.19 |
| 7,726,306 | B2 * | 6/2010 | Addington et al. | 128/203.12 |
| 8,109,266 | B2 * | 2/2012 | Addington et al. | 128/203.12 |
| 2001/0050086 | A1 | 12/2001 | Addington et al. | 128/898 |
| 2002/0121275 | A1 | 9/2002 | Johnson et al. | 128/200.22 |
| 2003/0079742 | A1 | 5/2003 | Giroux | 128/200.14 |
| 2003/0121517 | A1 * | 7/2003 | McFarland, Jr. | 128/200.14 |
| 2003/0136399 | A1 | 7/2003 | Foley et al. | 128/200.14 |
| 2003/0205229 | A1 | 11/2003 | Crockford et al. | 128/204.23 |
| 2004/0172010 | A1 | 9/2004 | Addington et al. | 604/890.1 |
| 2004/0181161 | A1 | 9/2004 | Addington et al. | 600/529 |
| 2004/0187864 | A1 | 9/2004 | Adams | 128/200.14 |
| 2004/0206351 | A1 * | 10/2004 | McFarland, Jr. | 128/203.12 |
| 2005/0081844 | A1 | 4/2005 | Grychowski et al. | 128/200.14 |
| 2007/0163572 | A1 | 7/2007 | Addington et al. | 128/200.14 |
| 2008/0004540 | A1 | 1/2008 | Nakao et al. | 600/529 |

OTHER PUBLICATIONS

Cates et al., "*Holding Chambers Versus Nebulisers for Inhaled Steroids in Chronic Asthma (Review),*" The Cochrane Collaboration, The Cochrane Database of Systematic Reviews 2006, Issue 1, pub 2, DOI: 10.1002/14651858, CD001491, pub 2, 23 pages.

Lasserson et al., "*Differences in Motor Activation of Voluntary and Reflex Cough in Humans,*" PubMed: Thorax. Aug. 2006; 61(8): 699-705.

\* cited by examiner

MEDICINE
FEED LINE
ENTERS
MIXING
CHAMBER

NEBULIZER HAVING FLOW METER FUNCTION

Related Applications

This application is a continuation of Serial No. 12/724,785 filed Mar. 16, 2010, now U.S. Pat. No. 8,109,266 which is based on provisional application Ser. No. 61/160,735, filed Mar. 17, 2009, and is a continuation-in-part of application Ser. No. 11/557,993, filed Nov. 9, 2006 now U.S. Pat. No. 7,726,306, which is a continuation-in-part of application Ser. No. 11/431,689, filed May 10, 2006, now U.S. Pat. No. 7,712, 466 which is a continuation-in-part of application Ser. No. 10/783,442, filed Feb. 20, 2004, now abandoned the disclosures of which are hereby incorporated by reference in their entirety.

FIELD OF THE INVENTION

The present invention relates to the field of nebulizers, and more particularly, this invention relates to intra-oral nebulizers.

BACKGROUND OF THE INVENTION

Inhalation is a very old method of drug delivery. In the twentieth century it became a mainstay of respiratory care and was known as aerosol therapy. Use of inhaled epinephrine for relief of asthma was reported as early as 1929, in England. Dry powder inhalers have been utilized to administer penicillin dust to treat respiratory infections. In 1956, the first metered dosed inhaler was approved for clinical use.

The scientific basis for aerosol therapy developed relatively late, following the 1974 Sugar Loaf conference on the scientific basis of respiratory therapy.

A more complete history of the development of aerosol therapy and the modern nebulizer is described in the 2004 Phillip Kitridge Memorial Lecture entitled, "The Inhalation of Drugs: Advantages and Problems by Joseph L. Row; printed in the March 2005 issue of Respiratory Care, vol. 50, no. 3.

The typically used modern nebulizer is delivered as a kit of seven plastic pieces, which are assembled prior to use to provide for delivery of the medication to a patient via inhalation. An exploded view of the seven pieces showing their relationship for assembly is given in FIG. 1. There is a mouthpiece 100 that is force fit onto one end of a T connector 110. Similarly, the other end of the T connector 110 is attached to a flex tube 120, also by force fit. The parts are such that the components can be assembled and disassembled with a simple twisting action. Nevertheless, when engaged and pressed together, the pieces form a substantially airtight seal. The bottom part of the T connector 110 is connected to a cup cover 130. That, too, is connected by pushing the cup cover onto the bottom part of the T connector in such a way that the airtight seal is formed. The cup cover 130 has a screen 135 that screens the material going into the T connector. There is a cup 150 for receiving the medicine to be nebulized. The cup also has a venturi projecting through the bottom.

In a typical use, a vial containing the medication for administration through the nebulizer is opened and poured into the cup 150 where it accumulates at the edges of the rounded bottom of the cup. The venturi is surrounded by a conical plastic piece through which it passes. The shape of the conical piece of the medicine cup 150 matches substantially the shape of the venturi cover 140. Once the medicine is poured into the cup, the venturi cover 140 is placed over the venturi and the filled medicine cup is screwed, using threaded portions on each piece, onto the cup cover 130. In this way, the medicine is held in place ready for administration.

In use, the bottom of the airline feeding the venturi in the medicine cup is attached to an air hose 160, to which is applied to a source of air pressure thus activating air flow through the venturi. By venturi action, the exhaust of the air flow through the small opening of the venturi results in a reduction in pressure on the downstream side of the air flow so that the medicine from the medicine cup is fed under positive pressure up in the interstices between the conical shape of the medicine cup and the venturi cover and is exhausted then through the screen 135 into the bottom of the T connector 110.

A patient is asked to inhale the aerosol mist provided through the cup cover screen into the air flow channel between the mouthpiece 100 and the flex tube 120. As a patient takes the mouthpiece 100 in their mouth, and inhales, air flows through the open end of the flex tube 120, through the T connector 110, picking up the aerosol medication and into the patients' air passages through the mouthpiece 100.

Table 8 of the Respiratory Care article, referred to above, page 381, lists the characteristics of an ideal aerosol inhaler as follows:

TABLE 8

| |
|---|
| Dose reliability and reproducibility |
| High lung-deposition efficiency (target lung deposition of 100% of nominal dose) |
| Production of the fine particles ≤5 μm diameter, with correspondingly low mass median diameter |
| Simple to use and handle |
| Short treatment time |
| Small size and easy to carry |
| Multiple-dose capability |
| Resistance to bacterial contamination |
| Durable |
| Cost-effective |
| No drug released to ambient-air |
| Efficient (small particle size, high lung deposition) for the specific drug being aerosolized |
| Liked by patients and health care personnel |

The standard nebulizer shown in FIG. 1, fails to achieve a number of these characteristics. Specifically, the nebulizer of FIG. 1 wastes medication during exhalation. Further, the particle size is often too large to reach the bottom of the lungs where the medication may be most needed. There is difficulty in estimating the dose of the drug being given to a patient and there is difficulty in reproducing that dose. There is a possibility of contamination when opening the initially sterile kit, poring medication into the cup, and assembling the pieces for use by a patient. There is also considerable inefficiency in the medication delivery, with much of it being deposited in the throat, rather than in the lungs.

Commonly assigned U.S. Patent Publication Nos. 2007/0163572 and 2007/0107725, and which are identified above as the incorporated by reference '993 and '689 applications, disclose intra-oral nebulizers in which the nebulizer places a venturi in close proximity to or inside a patient's oral cavity. One or more feed lines feed the medicine to a location proximate to a venturi. Medicines can be administered simultaneously to a patient. Air pressure is applied to the venturi to aid in nebulization.

When a patient performs a treatment with the nebulizer, it would be advantageous to determine if the patient's respiratory function has improved due to the use of the drug being administered. Also, it would be advantageous for the patient to use the nebulizer for respiratory exercise and incentive spirometry uses in which flow and pressure can be measured over time and pulmonary function testing performed.

SUMMARY OF THE INVENTION

In accordance with non-limiting examples, a nebulizer includes a main body comprising an air channel section and further comprising a mixing chamber and a venturi positioned to be placed within the patient's oral cavity and configured to receive medicine and air and mix the medicine and air within the mixing chamber and receive the air flow through the venturi and cause the medicine entering the mixing chamber to be atomized by the action of air flowing through the venturi. An air flow sensor is associated with the main body and configured to measure the air flow created by the patient's one of at least inhaling and exhaling air.

The air flow sensor in one non-limiting example is positioned within the air channel section and configured to measure air flow created by the patient's one of at least inhaling and exhaling air. A processor in another example is configured to process the measured air flow over time to determine a respiratory function of the patient. The processor is configured to process measured air flow over time to determine in another example a neurological deficiency in a patient based on air flow measurements derived from an involuntary reflex cough. For example, the neurological deficiency could be stress urinary incontinence and the processed measurements could be used to evaluate stress urinary incontinence in the patient.

In one example, the processor is formed as a handheld processing device that receives data regarding the measured air flow. A wireless module in another example is carried by the main body and transmits wireless signals containing data about the measured air flow created by the patient's one of at least inhaling and exhaling air. In yet another example, an air flow metering valve is positioned within the air flow channel and configured to adjust the resistance to air flow to a predetermined level for respiratory exercise training and incentive spirometry use. In yet another example, the flow sensor comprises a separate flow meter device removably attached to the main body and configured for use by a patient after nebulizing.

In yet another example, the mixing chamber is configured as a rainfall chamber and a diffuser is positioned within the rainfall chamber upon which the medicine that is nebulized impacts and configured to break up droplets of medicine expelled from the venturi into smaller sizes. In yet another example, a plurality of medicine receivers are on the main body, each shaped to match a shape uniquely associated with a different medicine receiver. The air channel section is configured to receive medicine from a medicine container that is received within the medicine receiver. Air curtain conduits are configured in another example to apply a curtain of air above and below the nebulized medicine and air to enhance penetration of nebulized medicine into the airway of the patient. The air sensor in an example is configured to measure air velocity, and in another example, is configured to measure air pressure.

A method of administering a medicine to a patient using a nebulizer is also disclosed. The steps comprise nebulizing the medicine by passing air through a fluid air channel section of a main body of the nebulizer comprising a mixing chamber and venturi that is positioned to be placed within the patient's oral cavity and configured to receive medicine and air and mix the medicine and air within the mixing chamber and receive the air flow from the venturi and cause the medicine entering the mixing chamber to be atomized by the action of air flowing through the venturi. The method further comprises measuring the air flow created by the patient's one of at least inhaling and exhaling air and processing the measured air flow over time to determine a respiratory function of the patient.

BRIEF DESCRIPTION OF THE DRAWINGS

Other objects, features and advantages of the present invention will become apparent from the detailed description of the invention which follows, when considered in light of the accompanying drawings in which:

FIG. 1 is an exploded view of a nebulizer kit of the prior art.

FIG. 2 is a perspective view of an improved nebulizer in accordance with one aspect of the invention.

FIG. 3 is a sectional view of the nebulizer of FIG. 2, cut along the centerline of the longitudinal axis.

FIG. 4 is a sectional view of the nebulizer of FIG. 2 showing a cut along the transverse axis at the air line.

FIG. 5 is an exploded view of the nebulizer of FIG. 2 in accordance with one aspect of the invention.

FIG. 6 is an assembled view of the nebulizer of FIG. 2 with a medicine vial in place for use.

FIG. 7 is a perspective view of a portion of the nebulizer shown in FIG. 2, showing an air line connection.

FIG. 8 is an embodiment of a nebulizer that has a pressurized gas canister connected to selectively activate the venturi of the nebulizer.

FIG. 9 is a view of the nebulizer of FIG. 8, showing insertion of another type of medicine dispenser.

FIG. 10 is a perspective view of the open end of the fluid/air channel section of the nebulizer, which interfaces with a fluid combiner and nozzle section and the distal diffuser end piece.

FIG. 11 shows a detailed side sectional view of the venturi, the mixing chamber and a diffuser.

FIG. 12 shows a detailed perspective view of the venturi, mixing chamber and diffuser shown in FIG. 11.

FIG. 13 shows one form of fluid feed from the medicine reservoir to the venturi and mixing chamber.

FIG. 14 shows an alternative form of fluid feed from the medicine reservoir to the mixing chamber.

FIG. 15 shows an improved nebulizer in accordance with one aspect of the invention, which utilizes four shape-keyed medicine sources with individual medicine feeds to the venturi and mixing chamber.

FIG. 16 shows an exemplary fluid/air channel section of the nebulizer of FIG. 15.

FIG. 17 is a perspective view of an alternative embodiment of a nebulizer in accordance with one aspect of the invention.

FIG. 18 is a side sectional view of the alternative embodiment of FIG. 17.

FIG. 19 is a side sectional view of the end of the nebulizer of FIG. 17 that engages the patient's mouth.

FIG. 20 is a sectional view of the nebulizer similar to that shown in FIG. 3 and showing an air flow sensor associated with the main body and a wireless module that includes a processor and transceiver that can receive measured air flow and wirelessly transmit data containing measured air flow to a handheld processing device in accordance with a non-limiting example.

FIG. 21 is a sectional view of the nebulizer such as shown in FIG. 4 and showing the flow sensors that are mounted within the air channel section of the nebulizer and in this example showing in greater detail an air flow metering valve positioned within the air flow channel at the outlet of the nebulizer in accordance with a non-limiting example.

FIG. 22 is a cross-sectional view showing the mixing end of a nebulizer that can be used to provide air curtains and showing an air flow sensor mounted at the mixing end of the nebulizer in accordance with a non-limiting example.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

The description relative to FIGS. 2-19 set forth much of the description in the above-identified and incorporated by reference '993 and '689 patent applications.

Figure 1:
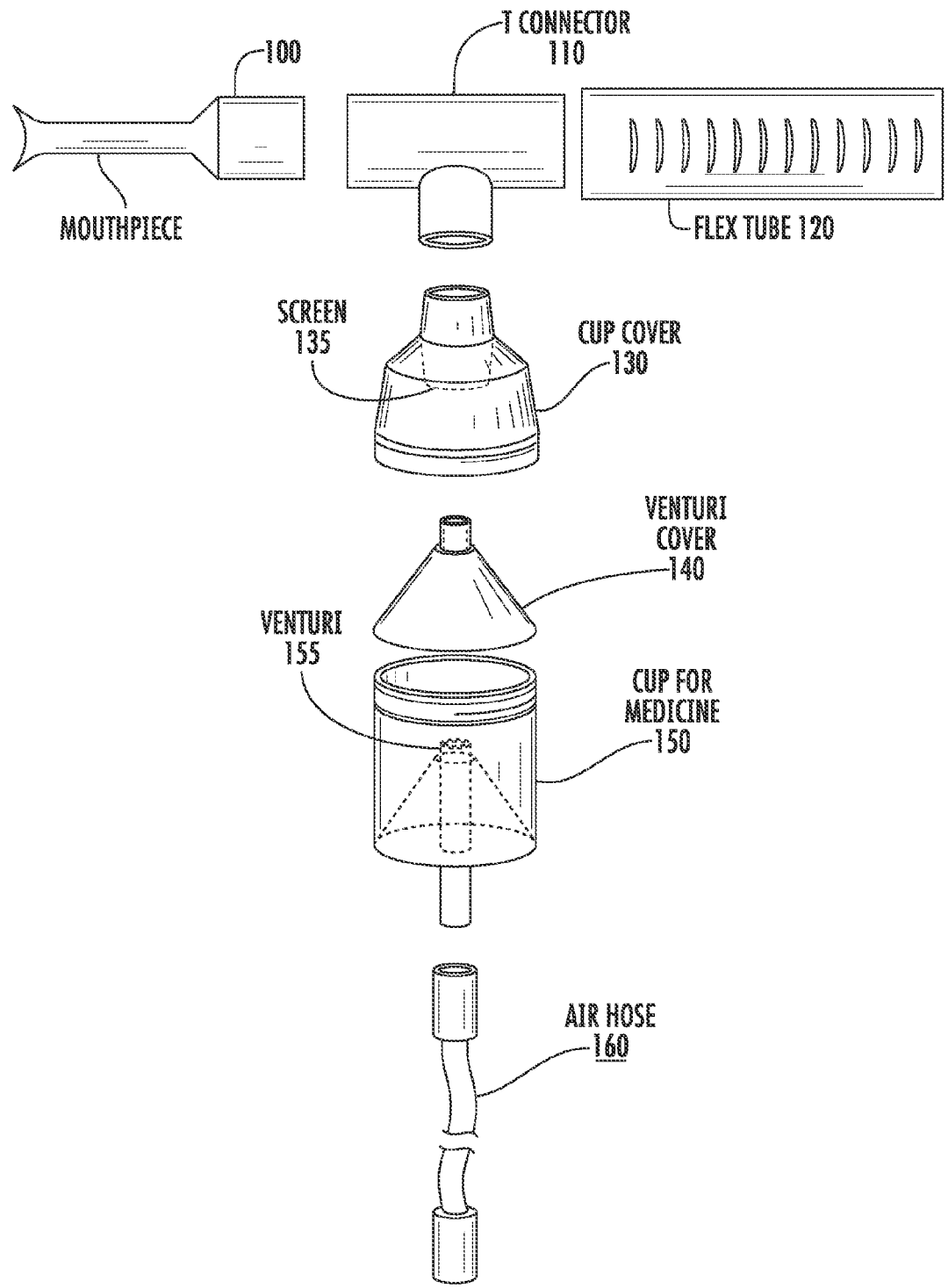
Figure 2:
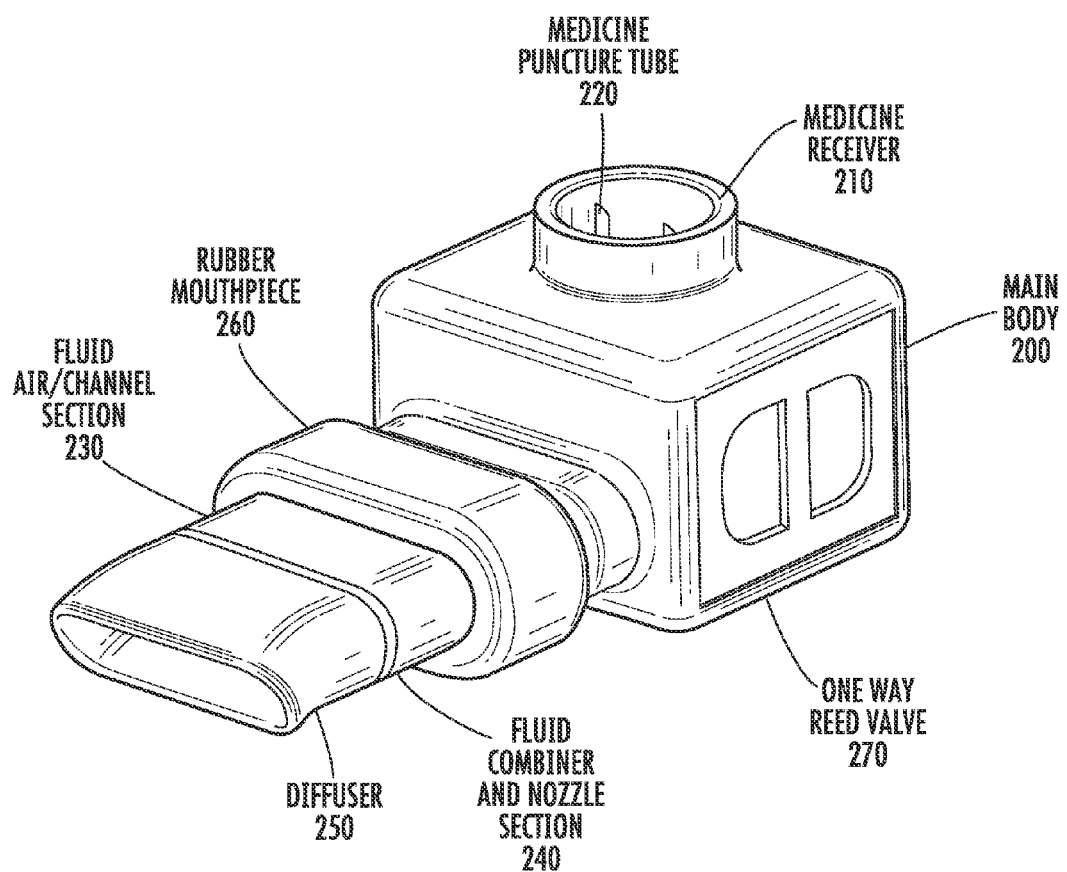

FIG. 2 is a perspective view of an improved nebulizer in accordance with one aspect of the invention. The nebulizer comprises a main body 200 which has a medicine receiver 210. Extending from the main body is a fluid air channel section 230. The fluid combiner and nozzle section 240 then mates the fluid air channel section 230 with the diffuser 250 as described more hereinafter. A rubber mouthpiece 260, the position of which can be adjusted, surrounds the nebulizer. The medicine receiver 210 is shaped to correspond to the shape of a medication vial or other medication container, which in this embodiment, can be punctured using the medicine puncture tubes 220 which are hollow and which permit the medication then to reach the venturi, discussed more hereinafter, utilizing, in most embodiments, a gravity feed, possibly supplemented with the venturi pressure differential.

Figure 3:
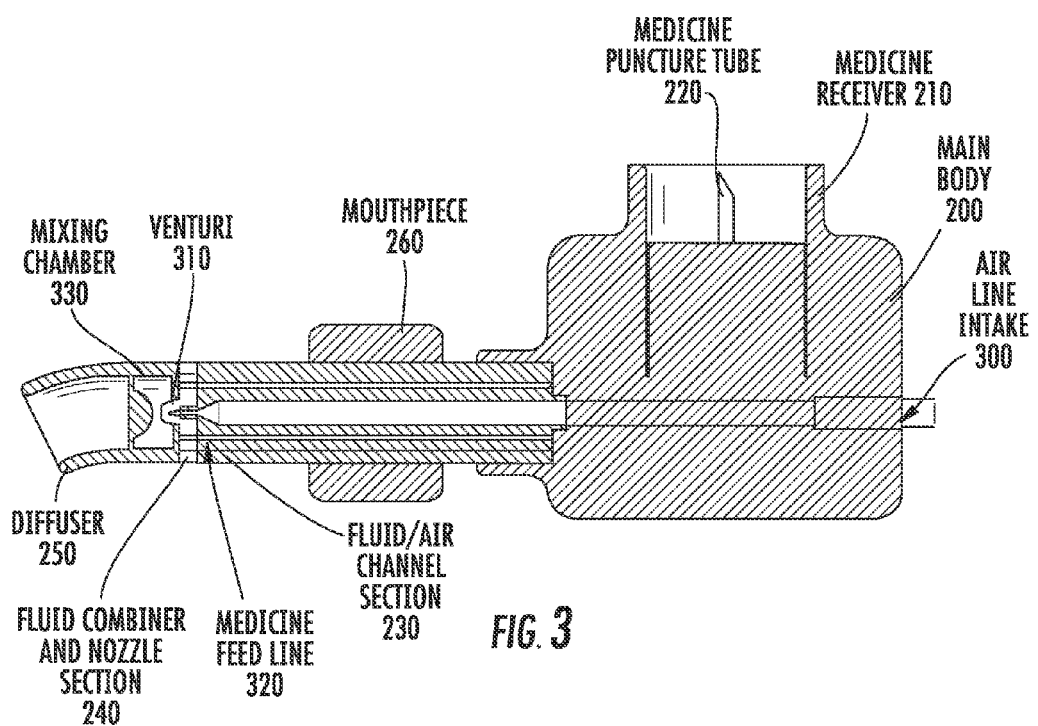

FIG. 3 is a sectional view of the nebulizer of FIG. 2, cut along the centerline of the longitudinal axis. Here one can see the path of the air from the air line 300 as it goes toward venturi 310. The medicine puncture tube 220 communicates with the medicine feed line 320 allowing the medication to flow from the medication reservoir into the medicine feed line into the mixing chamber 330 where it can be atomized by action of the venturi 310.

Figure 4:
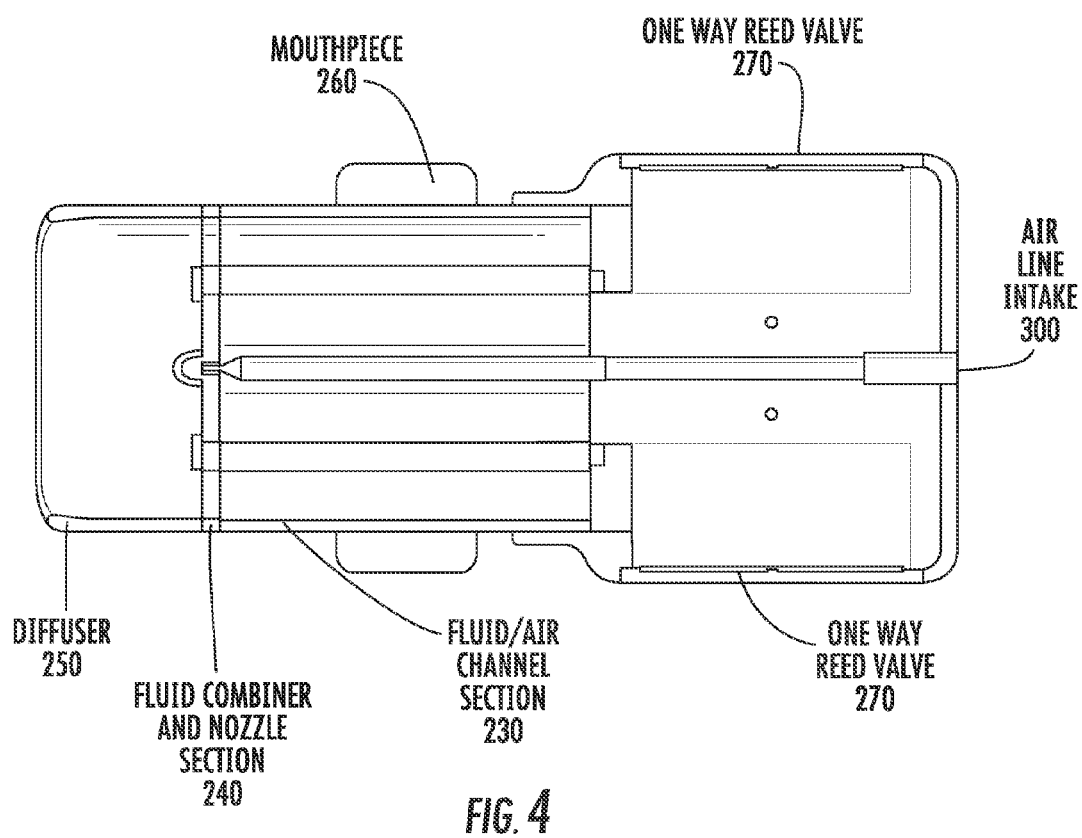

FIG. 4 is a sectional view of the nebulizer of FIG. 2 showing a cut along the transverse axis at the air line. This view shows the upper half of the nebulizer of FIG. 2 and again shows the air line 300 as it traverses the length of the nebulizer up to the venturi.

Figure 5:
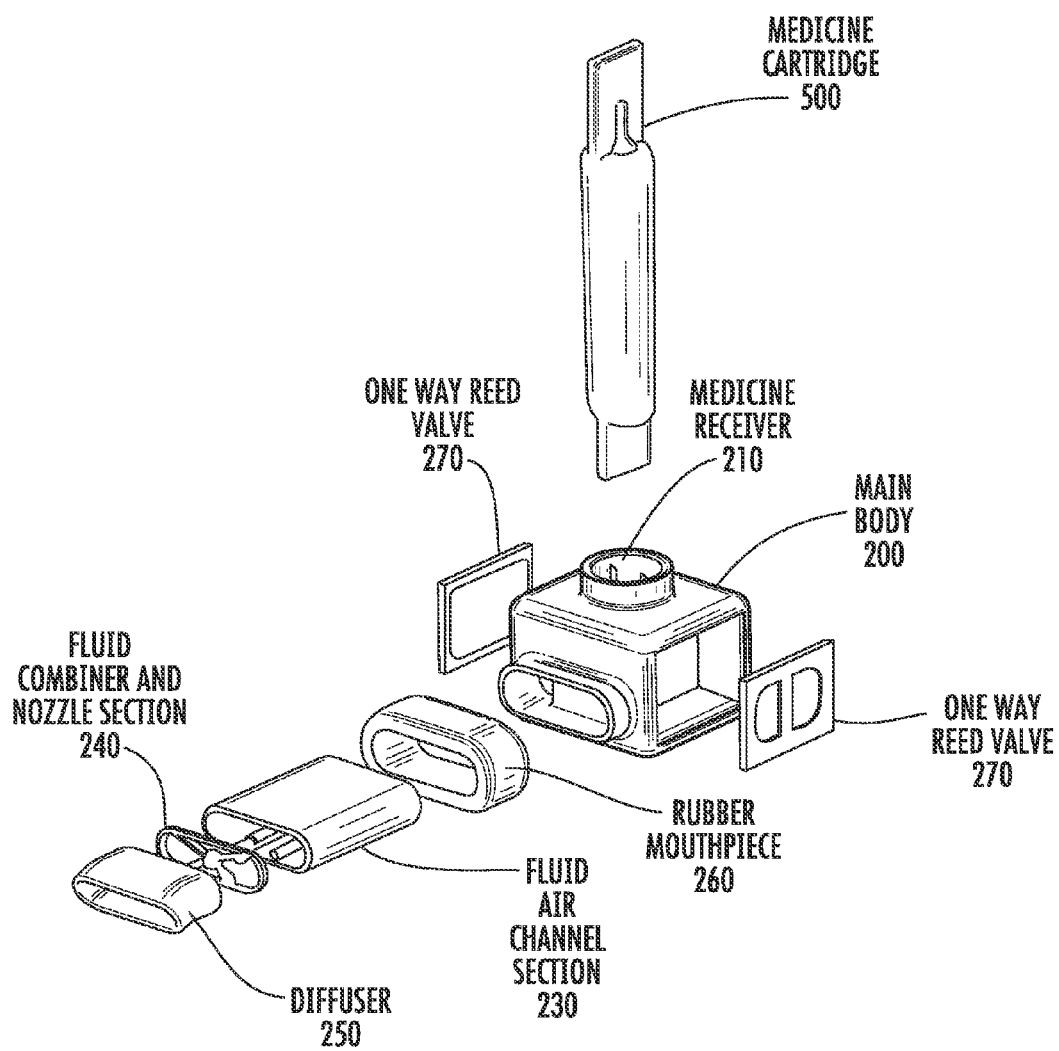

FIG. 5 is an exploded view of the nebulizer of FIG. 2 in accordance with one aspect of the invention. The nebulizer, as discussed previously, comprises a main body 200. On the main body is a medicine receiver 210 which is shaped to allow the medicine cartridge 500 to fit into the receiver. As the medicine cartridge 500 is inserted in the receiver, the medicine puncture tubes 220 in the medicine receiver 210 will puncture the medicine cartridge 500 allowing the medication to flow into the nebulizer for atomization in the mixing chamber, discussed hereinafter. The medicine puncture tubes 220 can either be a portion of a 22 gauge hollow needle which is press fit into the main body or plastic cast into the main body 200. The far end of the needle communicates with a medicine feed line discussed hereinafter. On either side of the main body 200 are one way reed valves 270, or openings which communicate with air passages in the fluid air channel section 230 to allow inhalation and exhalation by the patient. A fluid air channel section 230 communicates with the main body in such a way as to align with the air passages feeding the inlet and exhaust to openings or one-way reed valves 270. In addition, the fluid air channel section 230 communicates with the air line which is feeding the air to the venturi and with the medicine feed line or lines which bring medicine from the medicine cartridge or reservoir 500. The fluid combiner and nozzle section 240, interfaces between the fluid air channel section 230 in the diffuser 250 as described more in detail hereinafter.

Figure 6:
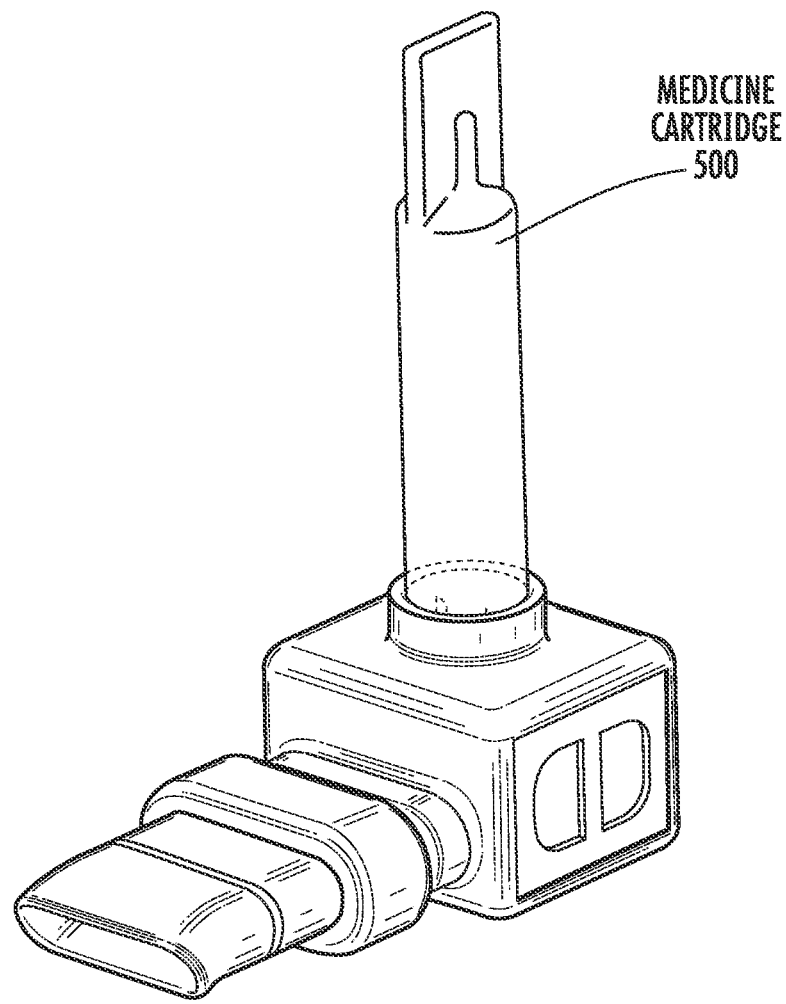

FIG. 6 is an assembled view of a nebulizer of FIG. 2 with the medicine vial in place for use.

Figure 7:
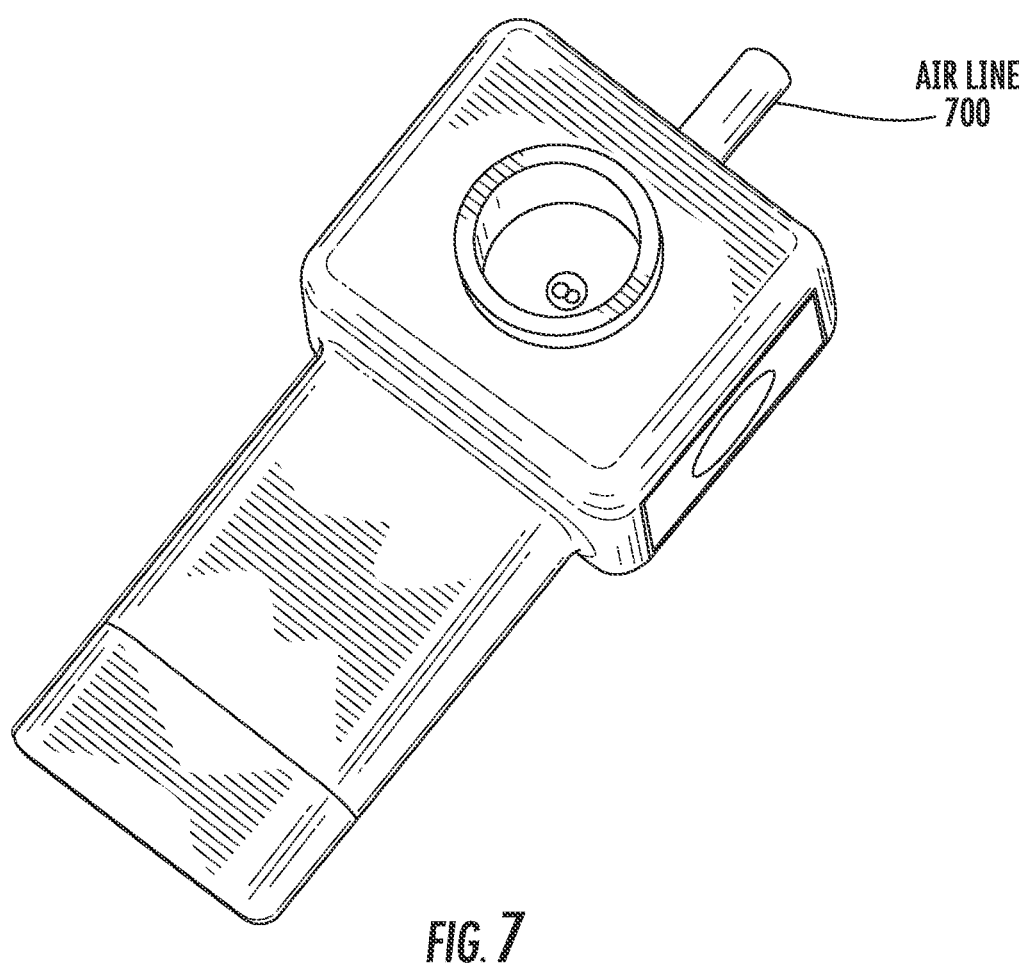

FIG. 7 is a perspective view of a portion of the nebulizer shown in FIG. 2, showing an air line connection.

Figure 8:
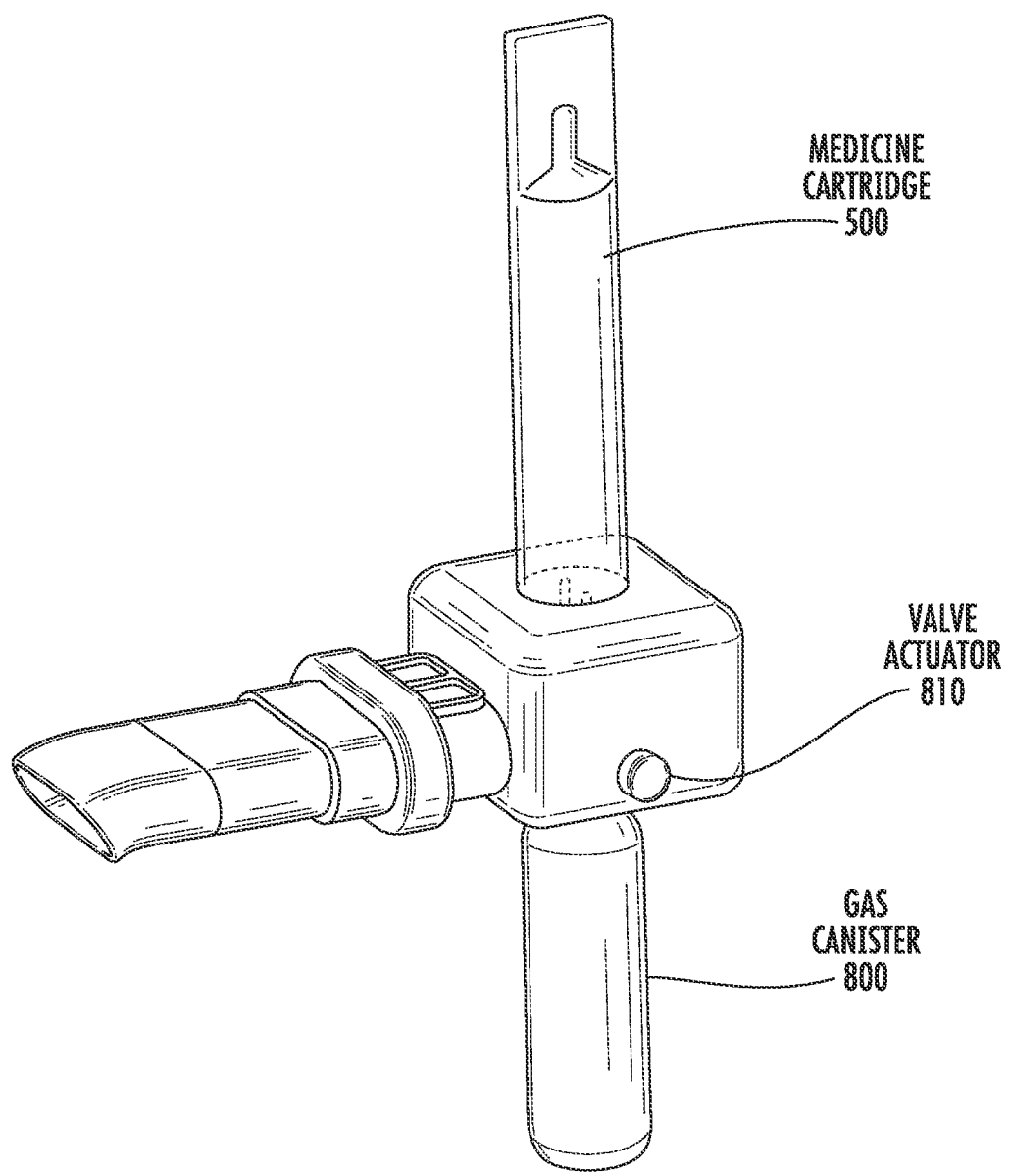

FIG. 8 is an embodiment of a nebulizer that has a pressurized gas canister connected to selectively activate the venturi of the nebulizer. Replacing an air line, which requires connection to a fixed source of air pressure, such as an oxygen tank or an air tank, is a gas canister 800 which is totally portable. The gas canister connects to the main body of the nebulizer, preferably with a screw on type connection. The passage from the exhaust of the gas canister to the venturi is through a press on release off type of valve which can be selectively activated, using the valve actuator 810 to provide the appropriate level of gas pressure to the venturi for mixing with the medication coming in from medication reservoir 500. In this particular embodiment the air inlet exhaust valves for inhalation and exhalation by the patient, instead of being positioned on each side of the nebulizer, are positioned on the top of the fluid air channel section 230.

Figure 9:
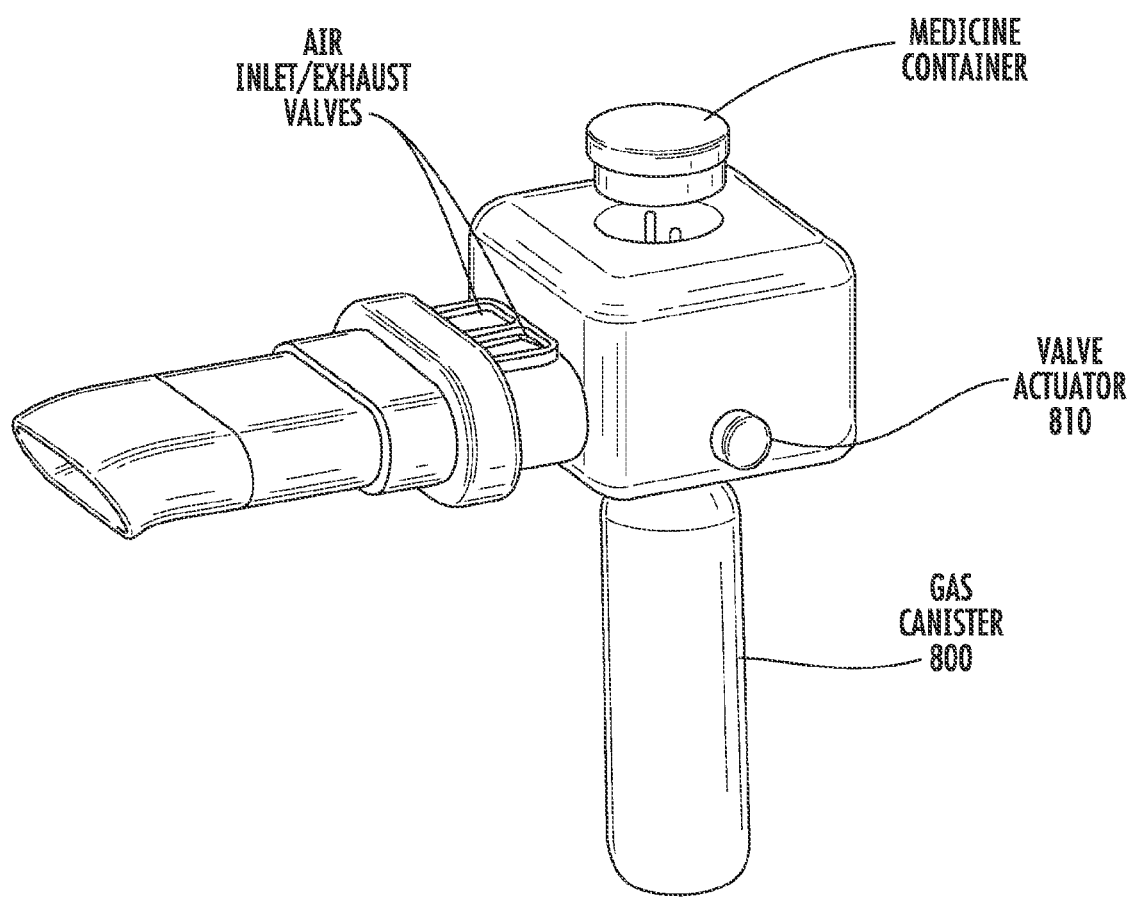

FIG. 9 is a view of the nebulizer of FIG. 8 showing insertion of another type of medicine container. In this case, the medicine container is shaped to be received by the medicine receiver, previously discussed, in the form of a small button, approximately the size of an antacid tablet, which contains an individual dose of the medication to be utilized. This permits a user to carry with him or her a number of such individual dose containers, optionally packed in a roll, which can be placed into the medicine receiver 210 to dispense the unit dose of medication for the particular patient utilizing the nebulizer. With the medicine in place, a patient can place the distal end of the nebulizer in his mouth, sealing his lips around the rubber mouthpiece 260 and synchronize inhalation with the activation of the valve actuator 810 which then activates the flow of gas from the pressurized gas container 800 through the venturi and the mixing chamber where the medicine from the medicine container is atomized by the action of the venturi and the diffuser plate as described more hereinafter.

Figure 10:
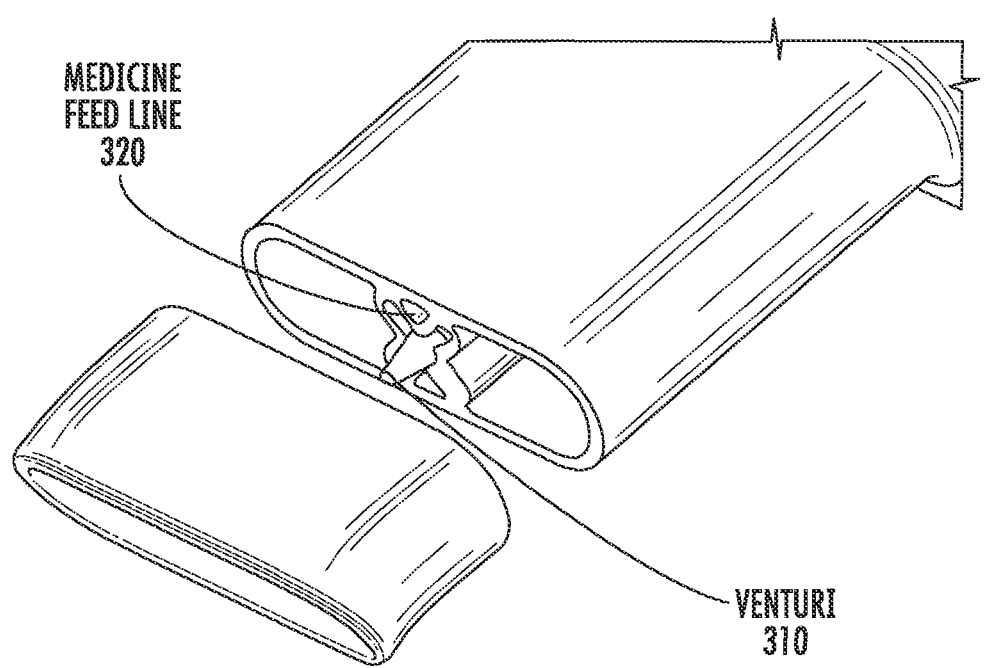

FIG. 10 is a perspective view of the open end of the fluid/air channel section of the nebulizer, which interfaces with a fluid combiner and nozzle section and the distal diffuser end piece.

As one can see in FIG. 10, the venturi 310 protrudes slightly beyond the end of the main body 200 into a mixing chamber to be shown hereinafter. Proximal to the venturi 310 is a medicine feed line 320.

Figure 11:
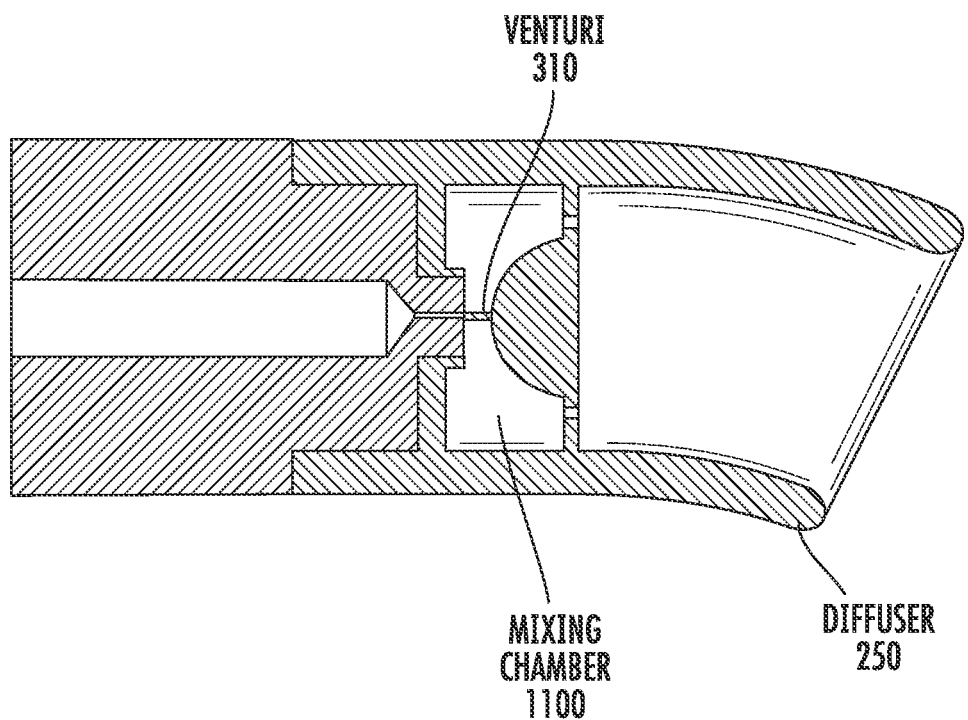

FIG. 11 shows a detailed side sectional view of the venturi, the mixing chamber and a diffuser. The venturi 310 extends into the mixing chamber 1100. The flow of air from the venturi is applied to a spherical diffuser element causing the medication entering the mixing chamber as shown hereinafter to be atomized by the action of the venturi flow.

Figure 12:
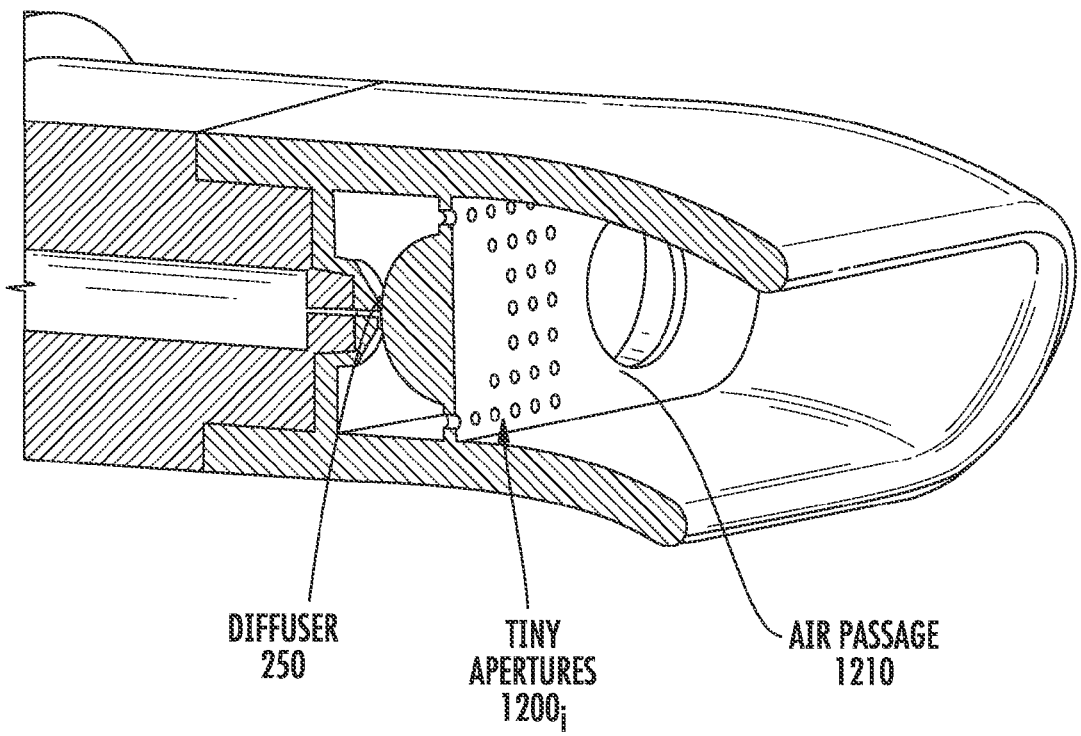

FIG. 12 shows a detailed perspective view of the venturi, mixing chamber and diffuser shown in FIG. 11. In this sectional view, one can see a plurality of tiny apertures 1200, through which droplets atomized in the mixing chamber by action of the venturi can pass, ensuring some maximum size of the droplets into the area through which the patient inhales and exhales. Since this is a cross section view, only one air passage 1210 is shown. However, there is a corresponding airflow aperture located symmetrically about the cut line. The one-way valves 270 are constructed so that the patient can inhale and exhale through one of the appropriate air passages 1210.

Figure 13:
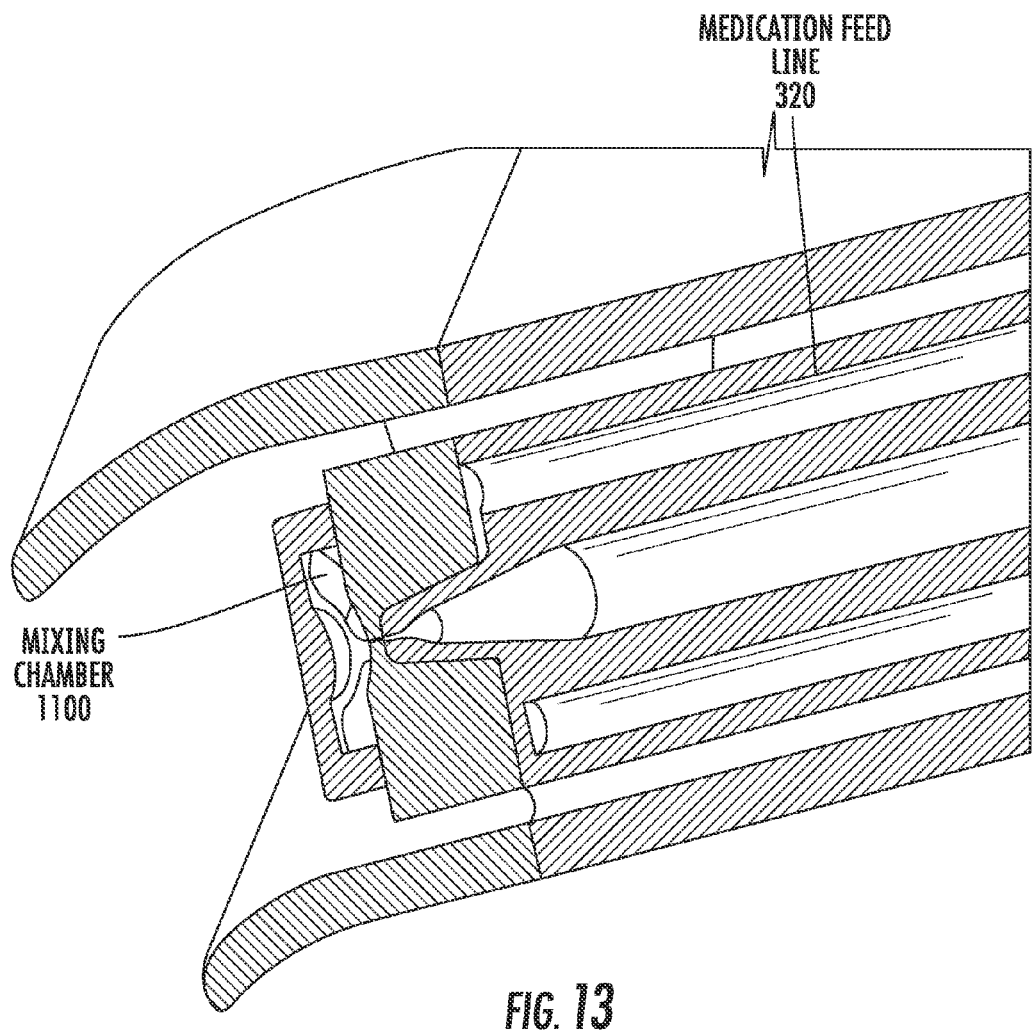

FIG. 13 shows one form of fluid feed from the medicine reservoir to the venturi and mixing chamber. In this particular embodiment, the medicine from the medicine feed line, which in this embodiment runs parallel to the air line feeding the venturi, ends at the fluid combiner and nozzle section 240. That piece fits over the nozzle, but is designed to allow flow of medication from the medicine feed line down into the proximity of the end of the venturi, exhausting in close proximity to the exhaust point of the venturi itself. The venturi action is such that the high speed flow of the air as it exits the venturi tip results in a considerably decreased pressure vis a vis the surrounding air pressure, which allows a partial vacuum to form which causes the medicine from the medicine feed line to enter into the mixing chamber by virtue of not only gravity feed, but of the pressure differential which results from the venturi action. The turbulence of the venturi feed interacting with the diffuser in close proximity with the medicine fed from the medicine feed line, results in atomization of the medicine in the mixing chamber.

Figure 14:
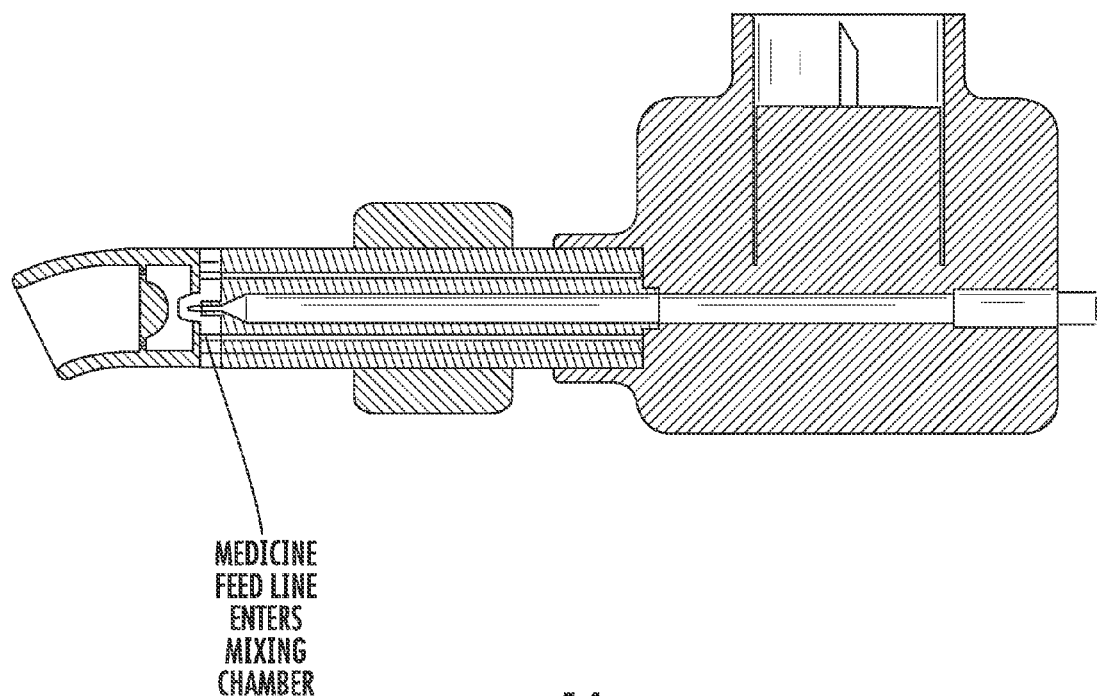

FIG. 14 shows an alternative form of fluid feed from the medicine reservoir to the mixing chamber. In this case, the medicine feed line enters the mixing chamber at a distance somewhat removed from the tip of the venturi. Nevertheless, the action of the venturi and the fuser in the mixing chamber is sufficient to atomize the medication for delivery to the patient.

Figure 15:
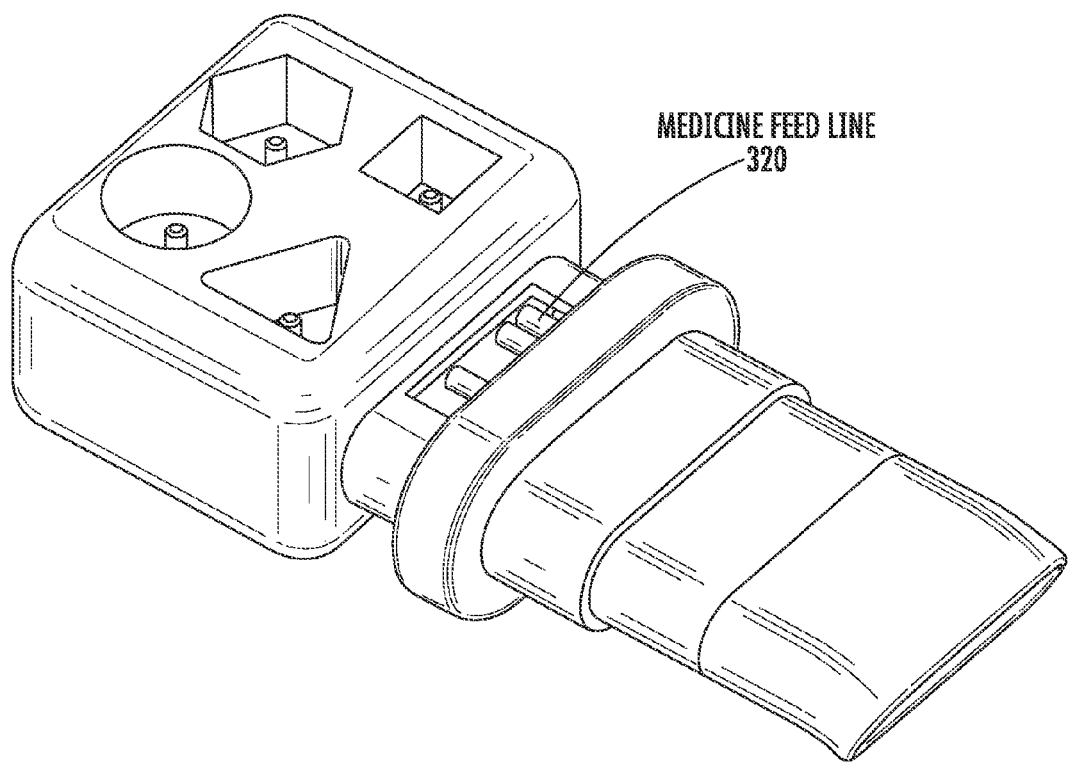

FIG. 15 shows an improved nebulizer in accordance with one aspect of the invention, which uses four shape-keyed medicine sources with individual medicine feeds to the venturi and mixing chamber. It is highly desirable to avoid a situation in which a patient might be given the incorrect medication. To insure the correct medicine is fed to the patient, each of the medicine containers or reservoirs are shaped having a unique shape that is specific for the medication to be administered. This provides a ready mechanism by which medical personal can visually confirm the correct medication being given to the patient. Each medication would be keyed to a particular shape and the shapes would become readily recognizable to medical personal resulting in fewer errors in administration.

It is also the case, that sometimes a plurality of medications would be administered simultaneously. In the case shown in FIG. 15, up to four medications can be administered simultaneously to a patient in the appropriate dosages. As noted above, each medicine container or reservoir can be configured to contain a unit dose of medication, each shaped according to its unique shape. As a result, the correct dosage can be applied to the patient and the dosage is reproducible. Three of the four medication feed lines are shown in FIG. 15, the fourth one not being visible by virtue of the manner of the depiction obscuring the fourth medicine feed line.

Figure 16:
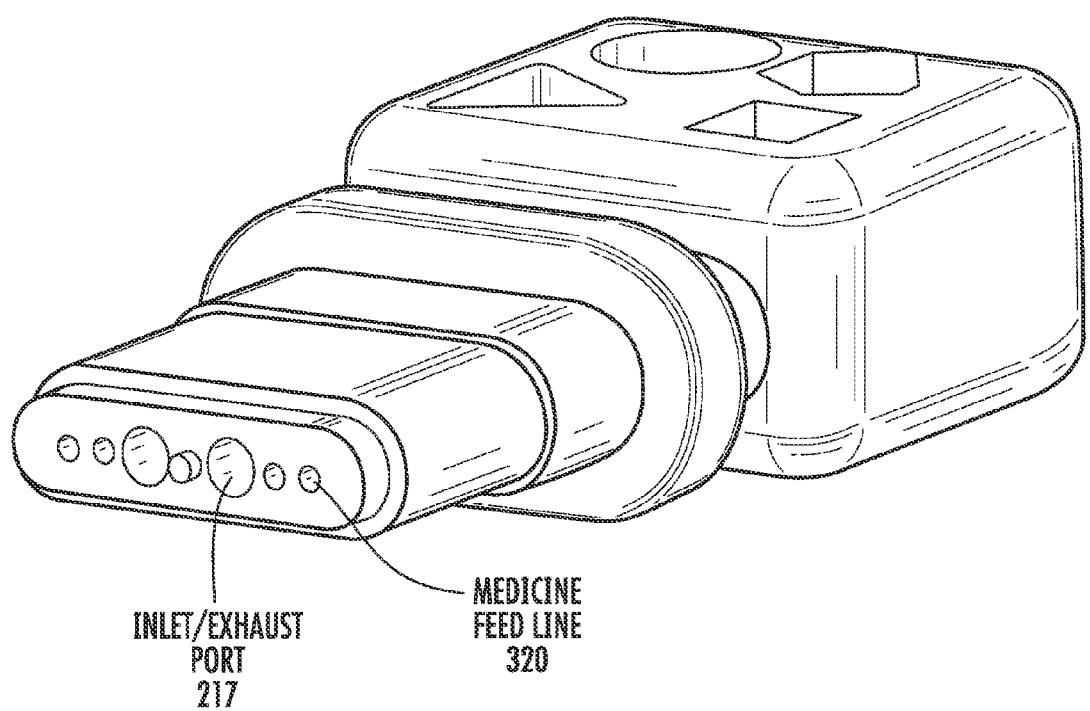

FIG. 16 shows an exemplary fluid air channel section of the nebulizer of FIG. 15. In the view shown in FIG. 16, there are four medicine feed lines, one from each of the key-shaped medicine receivers. There are also two larger ports which handle the inlet and exhaust from the patients breathing. In the version shown, the inlet and exhaust passages, the larger holes, feed respective inlet and output ports located behind the rubber mouthpiece shown in FIG. 16. The location of the inlet and outlet exhaust ports can be relocated as convenient without doing violence to the functioning of the nebulizer. For example, it is in some embodiments preferred to have the medicine feed lines located closer to the center line of the longitudinal axis of the nebulizer and have the air inlet/exhaust ports be located on either side of the four medicine feed lines. The latter configuration would be more appropriate where the air inlet/exhaust valves 217 are located on the side of the nebulizer, as shown, for example in FIG. 5, whereas the configuration shown in FIG. 16 might be preferable when the air inlet/exhaust ports are shown on the top of the fluid air channel section 230 as shown in FIG. 8.

Figure 17:
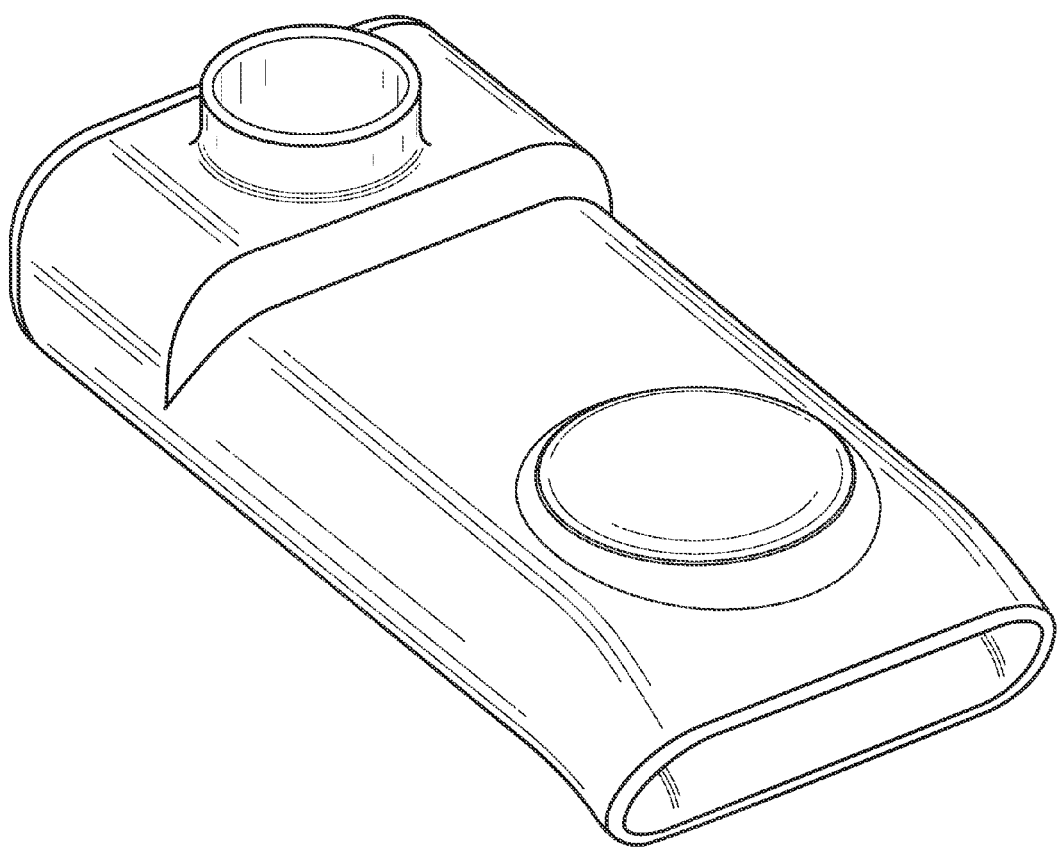

FIG. 17 is a perspective view of an alternative embodiment of a nebulizer in accordance with one aspect of the invention. In this view, in the upper left hand portion of the image is a medicine port for receiving a reservoir of medicine for utilization with the inhaler. At the proximal end the circular area shown indicates the location of the rainfall chamber as described more hereinafter. At the distal end, beyond the medicine port, but not shown in this view is an air intake for an air line feeding the venturi inside the nebulization rainfall chamber. The medicine for nebulizer can be filled directly into the reservoir or the nebulizer can come preloaded with the medicine.

Figure 18:
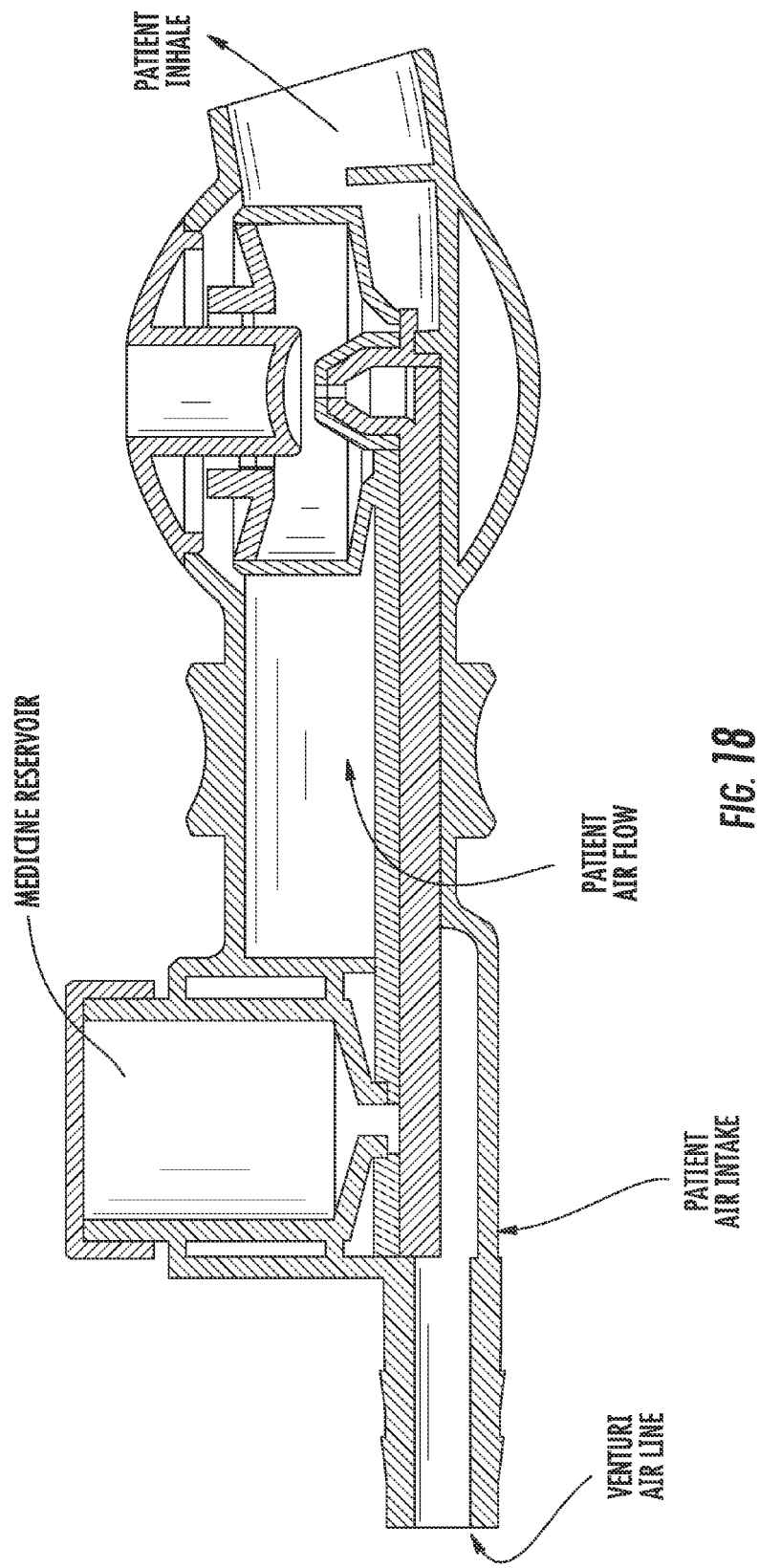

FIG. 18 is a side sectional view of the alternative embodiment of FIG. 17. In FIG. 18, the venturi air line is shown at the left end of the illustration. On either side of the venturi air line is a patient air intake port which allows air to be taken in at that port and fed through the body of the nebulizer as shown with the arrow indicating patient air flow direction. The medicine reservoir is shown as well as the patient inhale port for a patient to receive the medication. A cap covers the medicine reservoir. The cap can be screwed on, snapped on or otherwise locked on. The cap can be constructed so medicine can be injected into the reservoir through the cap.

Figure 19:
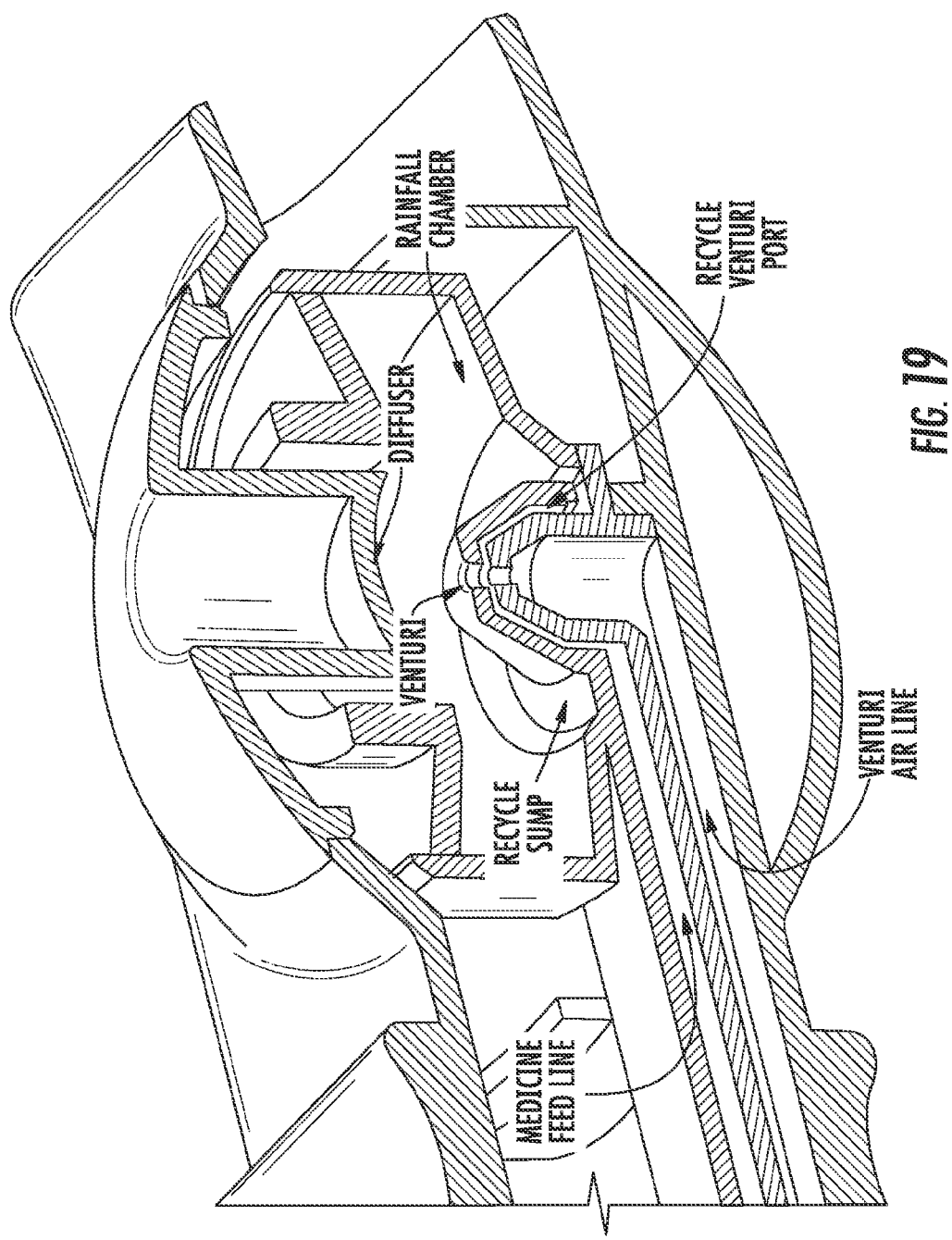
Figure 20:
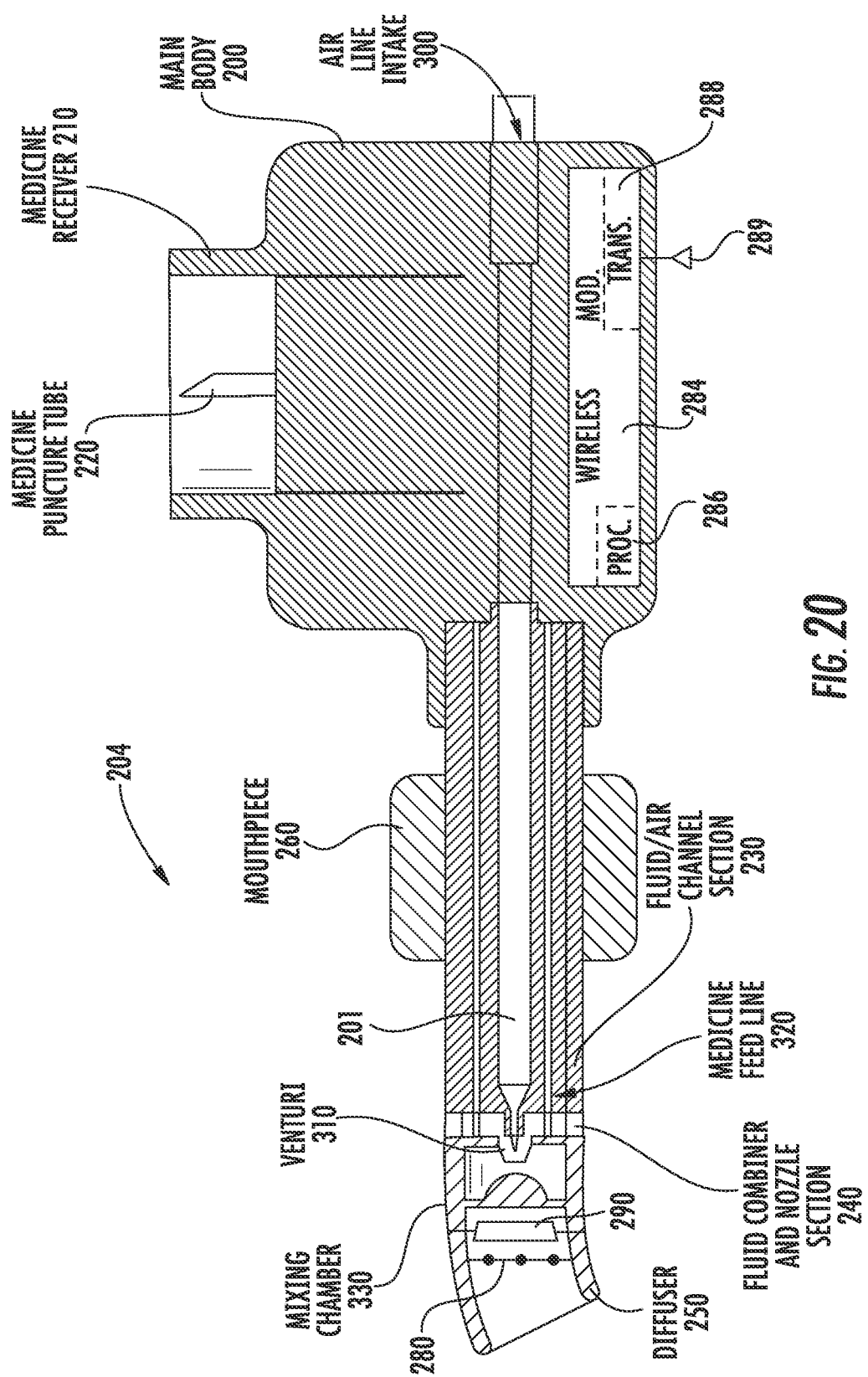
Figure 21:
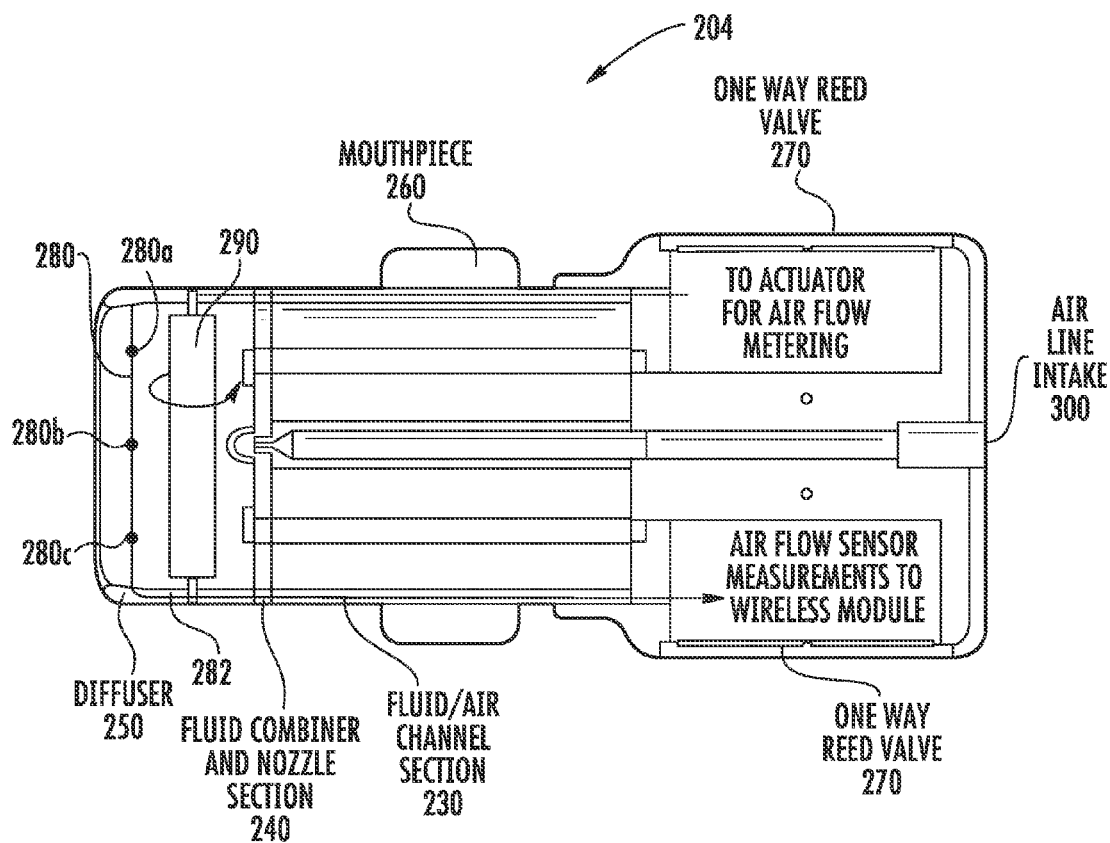
Figure 22:
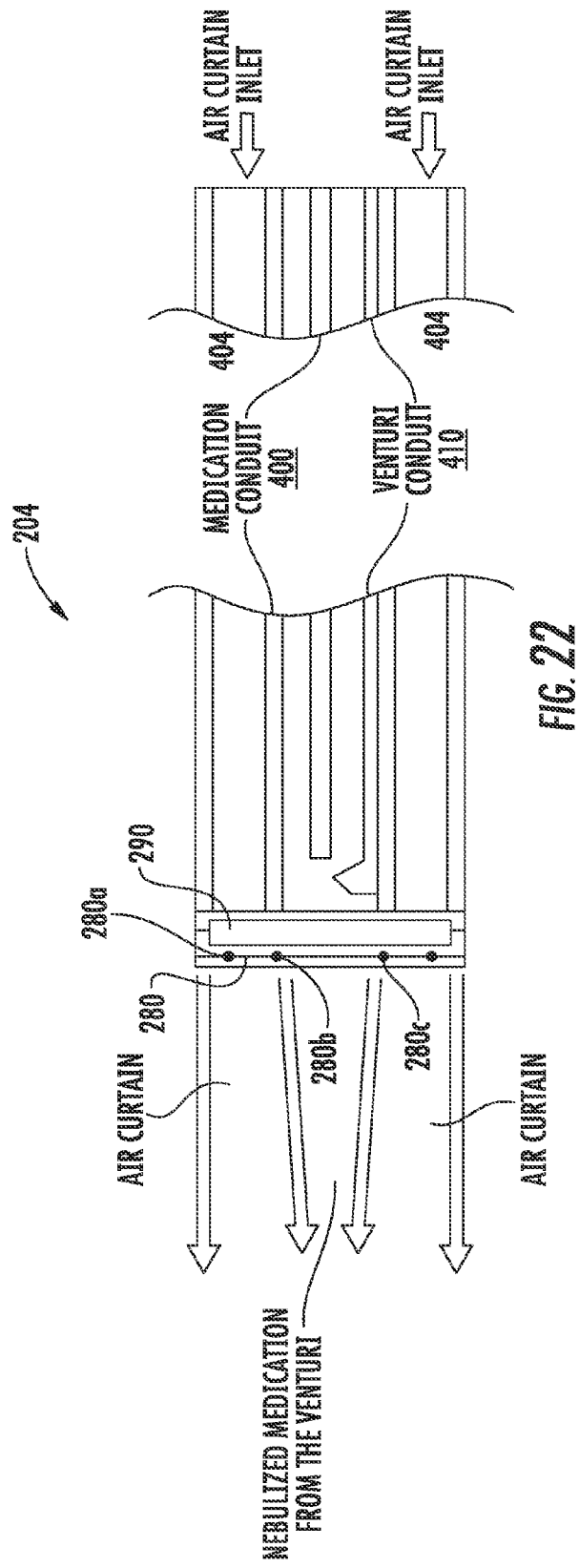
Figure 23:
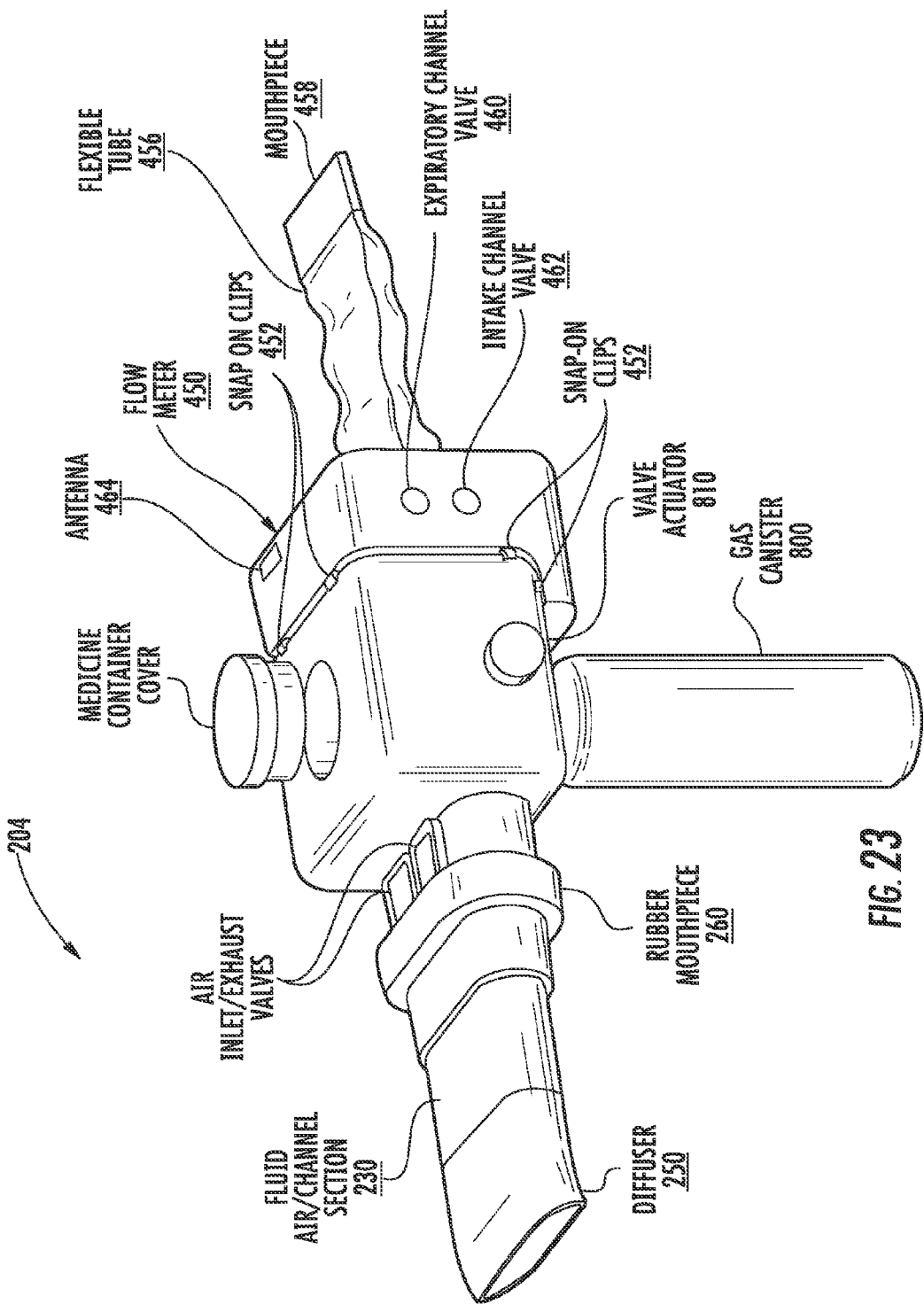
FIG. 23 is a perspective view of a nebulizer such as shown in FIG. 9 and showing a separate flow meter device removably attached to the main body and configured for use by a patient after nebulizing.
Figure 24:
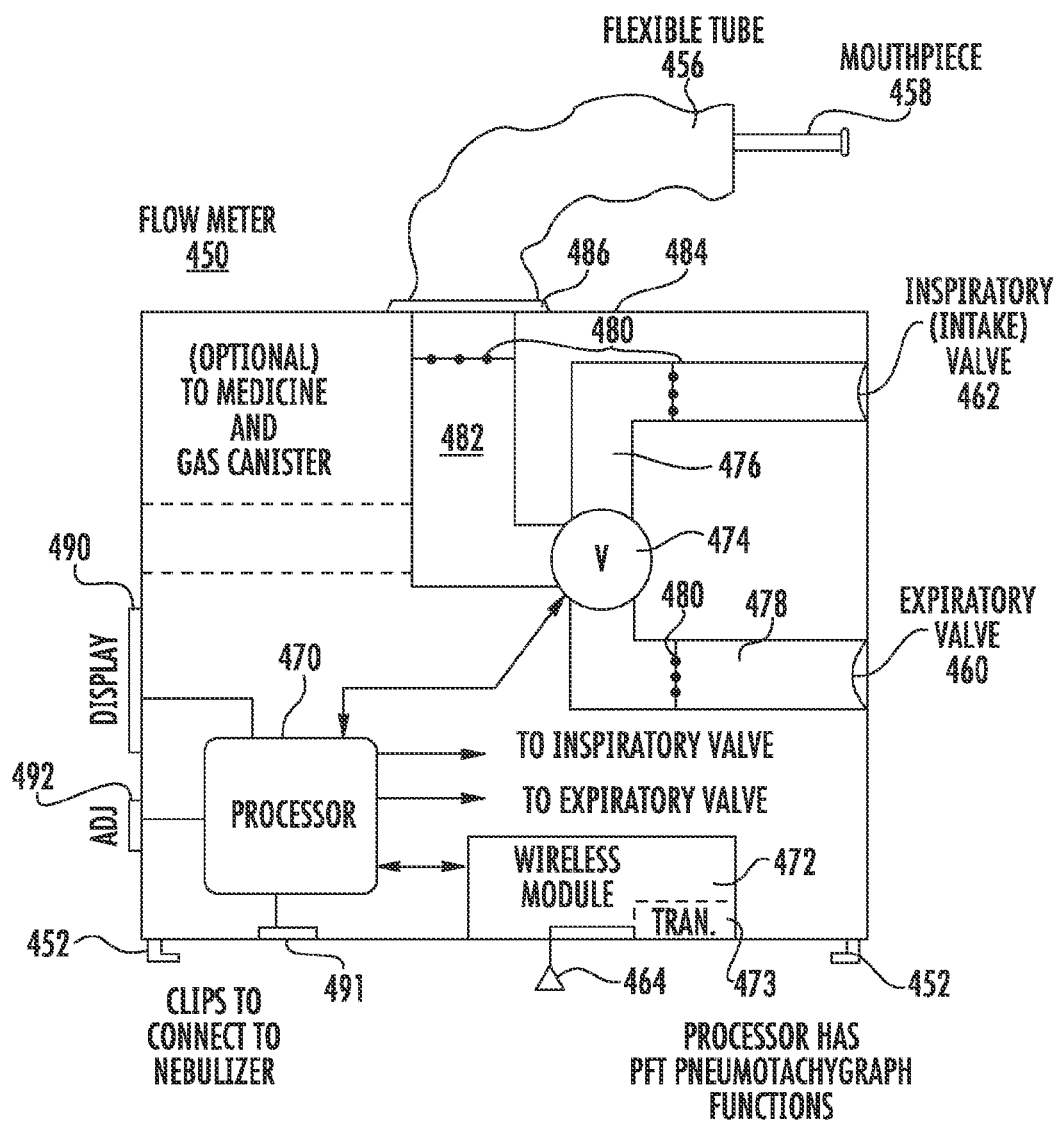
FIG. 24 is a block diagram showing basic components of the flow meter device that is removably attached to the nebulizer main body as shown in FIG. 23 in accordance with a non-limiting example.
Figure 25:
FIG. 25 is a fragmentary plan view of a handheld processing device that can be used in conjunction with the nebulizers as shown in FIGS. 20-24 and wirelessly receive data containing air flow measurements.
Figure 26:
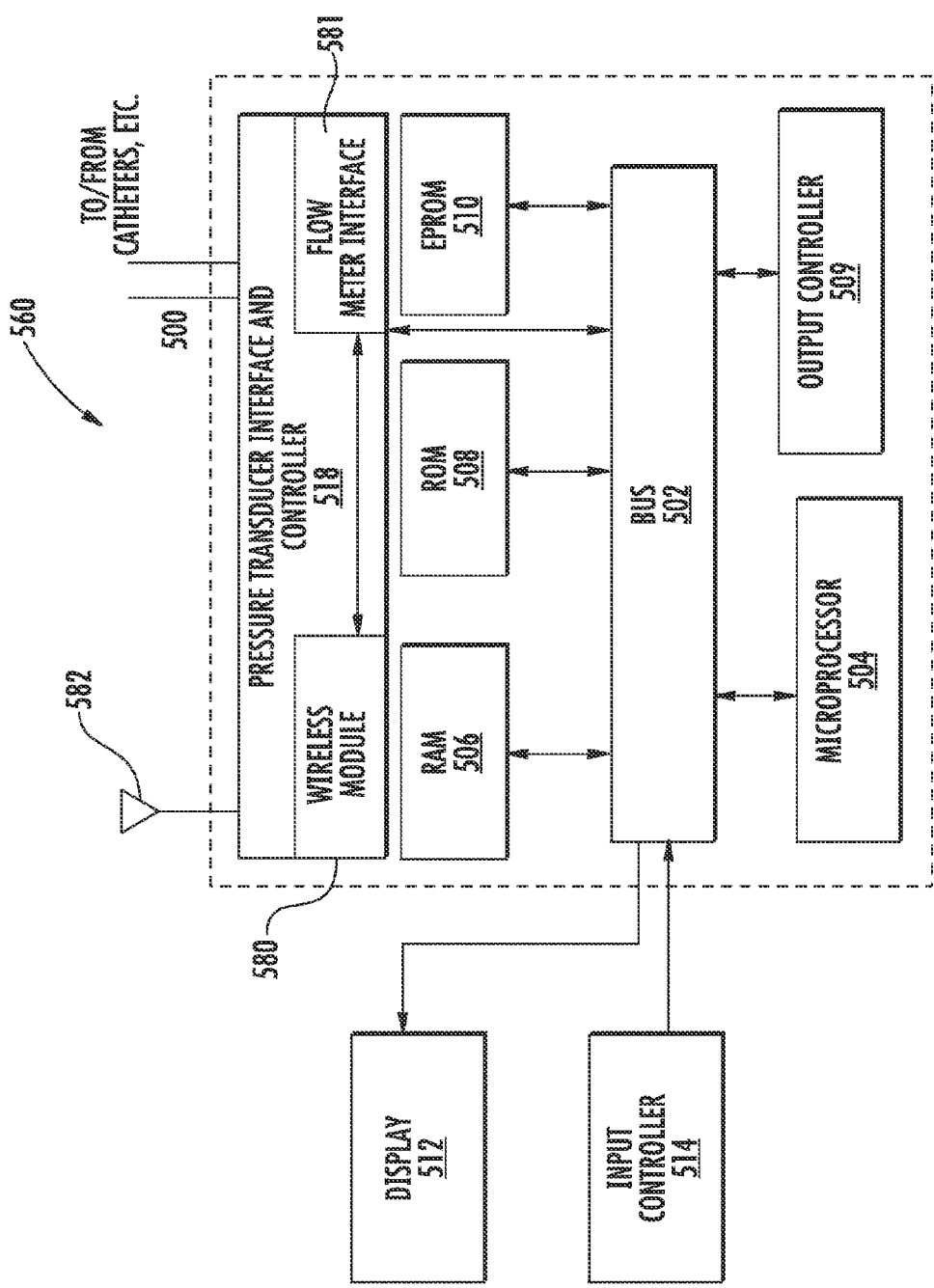
FIG. 26 is a block diagram showing basic components of the handheld processing device shown in FIG. 25 that can receive data from the nebulizer containing air flow measurements.

FIG. 19 is a side sectional view of the end of the nebulizer that engages the patient's mouth in accordance with one aspect of the invention, showing in more detail the rainfall chamber and the venturi and medicine feed lines. In FIG. 19, one can see the venturi nozzle in approximately the center of the illustration. Right beneath the venturi nozzle is a chamber which is fed by a venturi air line, indicated at the lower portion of the figure to the left of the venturi chamber. Parallel to the venturi airline and located somewhat displaced above the venturi air line is the medicine feed line. Medicine from the reservoir flows through the medicine feed line and through a relatively small opening just prior to the venturi in order to dispense medication into the air flow of the venturi. The venturi effect causes a reduction in pressure which causes the medicine to flow from the reservoir through the medicine feed line and into the venturi space where it is mixed with the air in traditional venturi fashion. The medicine that is nebulized by action of the venturi is expelled from the venturi port in an upward direction toward the diffuser. The diffuser in this case, is shown as textured. It is not necessary that it be textured but texturing may facilitate the break up of the droplets from the venturi into smaller sizes. As the droplets from the venturi bounce off the diffuser and break up, the sizes may not be totally uniform. The air pressure, the feed rate, the velocity with which droplets impact the diffuser and other well known factors can facilitate production of droplets of desired sizes. In fact, droplets can be generated utilizing this arrangement in sizes less than 0.1 microns. Nevertheless, larger droplets may coalesce as they diffuse throughout the rainfall chamber space. As droplets coalesce, they become larger and fall toward the bottom of the chamber where medication that is not utilized is gathered in a recycle sump. Medication found in the recycle sump, is recycled through the recycle venturi port to the proximity with the venturi intake to be reutilized. In this manner, very little medication is wasted and the amount of medication delivered to the patient can be tightly controlled.

When the patient places his mouth on the patient inhale port to the upper right of the image shown in FIG. 19, air from the patient inhale air path will circulate over the rainfall chamber and around the diffuser causing the extraction of droplets from the rainfall chamber for delivery to the patient. Note that the patient inhale air path may go not only over the rainfall chamber but around it to either side with the actual sizing depending upon the need for the amount of air flow to be delivered to the patient during administration of medication.

Returning again to Table 8 of the Respiratory Care article, discussed above, one can see that the invention has many of the characteristics of an ideal aerosol inhaler system as described there.

Dose reliability and reproducibility is enhanced by using unit dose medicine containers. High lung-deposition efficiency is vastly improved over the prior art because the venturi is located near or preferably inside the oral cavity. Very fine particles can be produced in accordance with the invention. The simplicity of use is enhanced by the use of a portable pressurized gas container and value actuation mechanism. The short treatment time is enhanced because the assembly of a seven-piece kit is not required. All that is required is that the medication be inserted into the medicine receiver and the actuator valve for the pressurized gas container is activated to deliver the medication. The nebulizer in accordance with the invention is a smaller size and easier to carry than the seven piece kit. The nebulizer of the invention has multiple dose capabilities, depending on the size of the medicine reservoir. The nebulizer of the invention is resistant to bacterial contamination, because the medication vials do not need to be opened and poured into an open cup as in the prior art. Nevertheless, it is possible to configure the nebulizer of the invention to utilize a cup that can be opened and to pour the medication into the cup as has been done in the past by simply making the medication reservoir with a screw off or pressure fit lid which will allow the medication to be put into the cup as it has been done in the past with the seven piece plastic kit. The nebulizer of the invention is durable and cost effective. Much less of the medication is released to the ambient air by virtue of the positioning of the venturi well within the oral cavity.

FIG. 20 shows a nebulizer 204 that includes the main body 200 having an air channel section 201 that is formed by the air line intake 300 and fluid/air channel section 230 and related sections of the main body as illustrated and including a mixing chamber 330 and venturi 310 positioned to be placed within close proximity or within the patient's oral cavity in this non-limiting example and configured to receive medicine and air and mix the medicine and air within the mixing chamber and receive the air flow through the venturi and cause the medicine entering the mixing chamber to be atomized by the action of air flowing through the venturi. In this embodiment, an air flow sensor 280 is associated with the main body, and in this example at diffuser 250, and configured to measure the air flow created by the patient's one of at least inhaling and exhaling air. In this example, the air flow sensor 280 is positioned within the air channel section 330 and as illustrated at the exit side of the mixing chamber within the diffuser such that air flow is measured when the patient is at least one of inhaling and exhaling air through the diffuser in this example.

The air flow sensor 280 senses and measures the air flow and sends a signal through communications signal lines 282 (shown in FIG. 21) back to a wireless module 284 positioned in the main body 200. The wireless module 284 in this example includes a processor 286 and wireless transceiver 288 such that the signals from the air flow sensor 280 are processed and in this example wirelessly transmitted through an antenna 289 (which could be a conformal antenna positioned on the main body 200) to a handheld processing device 560 such as shown in FIG. 25 and with its processing capability illustrated in block diagram at FIG. 26. The outlet at the diffuser on the exit side of the mixing chamber in this example chamber includes an air flow metering valve 290 positioned within the air flow channel and configured to adjust the resistance to air flow to a predetermined level for respiratory exercise training and incentive spirometry use. In this example, the air flow metering valve 290 is formed as a baffle or similar mechanism that can be adjusted to vary the amount of air flow resistance. The adjustment can be indexed such that any adjustment and air flow resistance can be predetermined, for example, using a manual adjustment or servo drive (actuator) for adjusting the valve. The air flow sensor 280 in this non-limiting example is shown as a number of air flow sensor members 280*a*, 280*b*, 280*c* adjacent the air flow metering valve 290. The sensors could be positioned in an example on the air flow metering valve. The air flow metering valve 290 in an example includes a small drive mechanism such as an actuator attached thereto, allowing adjustments to be made based upon a signal such as from the processor 286 and feedback signal from the air flow sensor to adjust and vary the amount of resistance to air flow for respiratory exercise training and incentive spirometry use. The valve 290 can also in one example be manually adjusted by a patient and include settings to aid in adjustment as noted before.

In a non-limiting example, the handheld processing device 560 is configured to process the measured air flow over time to determine a respiratory function of the patient. This device 560 is also configured in another example to process measured air flow over time to determine a neurological deficiency in a patient based on air flow measurements derived from an involuntary reflex cough. For example, the voluntary cough and involuntary reflex cough test as disclosed in commonly assigned U.S. patent application Ser. No. 11/608,316 filed Dec. 8, 2006; and U.S. patent application Ser. No. 12/643,134 filed Dec. 21, 2009; and U.S. patent application Ser. No. 11/550,125 filed Oct. 17, 2006; and U.S. patent application Ser. No. 12/643,251 filed Dec. 21, 2009, all the disclosures which are hereby incorporated by reference in their entirety, set forth details of voluntary cough testing and involuntary reflex cough testing in which the nebulizer as described in the instant application can be used to aid in the type of testing as set forth in those incorporated by reference applications. Such testing is advantageously used to diagnose stress urinary incontinence as a non-limiting example.

FIG. 22 shows a modified nebulizer such as the type disclosed in commonly assigned U.S. patent application Ser. No. 11/611,425 filed Dec. 16, 2006 as U.S. Patent Publication No. 2007/0137648, the disclosure which is hereby incorporated by reference in its entirety. This application shows air curtain inlets created by air curtain conduits 404 that are used to supply a curtain of air above and below the nebulized medicine and air passing through medication conduit 400 and to enhance penetration of nebulized medicine into the airway of the patient. The air flow sensor 280 is positioned at the exit end of the nebulizer 204 as illustrated and in this example includes the air flow metering valve 290 as illustrated and incorporates a manual or automatic adjustment mechanism such as an actuator as may be needed.

It should be understood that different types of air flow sensors 280 can be used. It is possible to design the air flow sensor 280 as a mass air flow sensor that converts the amount of air drawn or expelled into and out of the nebulizer into a voltage signal. Different types of mass air flow sensors could be used such as a vane air flow meter, including using any necessary MEMS technology or using a Karmen vortex or a semiconductor based MAF sensor. It is possible to use a hot wire MAF sensor such as a thermistor, platinum hot wire or other electronic control circuit to measure temperature of incoming air, which is maintained at a constant temperature in relation to the thermistor by an electronic control circuit. As heat is lost, electronic control circuitry can compensate by sending more current through the wire. This is only one example. The wire typically will be kept cool enough such that the temperature does not impact a patient. The hot wire can be placed further into the diffuser and/or main body within the air channel. It is also possible to use an Intake Air Temperature (IAT) sensor.

Another possible air flow sensor is a vane air flow meter that includes basic measuring and compensation plates and other potentiometer circuits. In another example, the air flow sensor uses a "cold wire" system where an inductance of a tiny sensor changes with the air mass flow over that sensor as part of an oscillator circuit whose oscillation frequency changes with sensor inductance. In another example, the flow sensor is an electronic membrane placed in the air stream that has a thin film temperature sensor such as printed on an upstream side and another on the downstream side and a heater in the center of the membrane that maintains a constant temperature similar to the hot-wire. Any air flow causes the membrane to cool differently at the upstream side from the downstream side and this difference indicates the mass air flow. MEMS technology can be used such as MEMS sensors. In this type of sensor, a MEMS sensor has a silicon structure and sometimes combined with analog amplification on a microchip. It includes an analog-to-digital converter on a chip in another example and can be fused with analog amplification and the analog-to-digital converters and digital intelligence for linearization and temperature compensation. The MEMS testing in one example is used for an actuator to control the valve 290.

It should be understood that although the air flow sensor is shown located at the discharge end of the nebulizer at the diffuser on the exit side of the mixing chamber, other locations and positions for the air flow sensor or number of air flow sensor members are possible as well as the valve 290.

It should also be understood that the nebulizer using the waterfall chamber as shown in FIGS. 17-19 also in an example has the flow meter function as described and includes the air flow sensor and wireless module as illustrated in FIGS. 20 and 21 and can be positioned in different locations within that device. The air flow sensor can be located at the discharge end on the exit side of the rainfall chamber or other locations in which the air flow can be measured. The valve 290 is also included in another embodiment and includes an actuator in yet another embodiment.

Air flow can be measured in pounds per second (lbs./sec.) and operate for pulmonary function testing calculations and incentive spirometry use. The nebulizer in this example can work as a differential pressure transducer and connect to a pneumotachygraph (or have a self-contained chip with such function) to record the velocity of respired air. It is possible to process associated data as air flow, air pressure, air resistance, and other Pulmonary Function Testing (PFT) results for respired air and data results from voluntary cough (VC) and involuntary reflex cough testing (iRCT). The pulmonary function testing can use spirometry to assess the integrated mechanical function of the lungs, chest wall and respiratory muscles and measure the total volume of air exhaled from a full lung for total lung capacity and empty lungs as residual volume. The Forced Vital Capacity (FVC) can be measured and a forceful exhalation ($FEV_1$) can be repeated. Spirometry can be used to establish baseline lung function, evaluate dyspnia, detect pulmonary disease and monitor effects of therapies used to treat respiratory disease and evaluate respiratory impairment and evaluate the operative risk and perform surveillance for occupational-related lung disease. Pulmonary function testing can be used to determine how much air volume is moved in and out of the lungs and how fast the air in the lungs is moved in and out. This testing can determine the stiffness of the lungs and chest wall for compliance. The flow meter function using the air flow sensor and the associated air flow metering valve together with any processing capability can be used for Inspiratory Muscle Training (IMT) to provide consistent and specific pressures for inspiratory muscle strength and endurance training. The adjustable valve or other adjustable mechanism can ensure consistent resistance and be adjustable such as manually or through microprocessor control for specific pressure settings. It is possible to use the same nebulizer for exercise treatments and therapy and spirometer treatments. The handheld processing device 560 captures the data and can be marketed together with the nebulizer and any necessary catheters for reflex cough testing as a kit. The pneumotachygraph function can be placed in a single chip within the nebulizer or as a separate flow meter device explained below relative to FIGS. 24 and 25 and connected to the nebulizer. Data containing air flow measurement results can be wirelessly transmitted to the handheld processing device or other processor.

The nebulizer also operates in a non-limiting example as a differential pressure transducer. If the nebulizer is to measure voluntary cough or the involuntary reflex cough, an air channel can be connected to the medicine and gas canister (for tartaric acid in one example) and measure the voluntary cough and involuntary reflex cough for in-phase duration from the time from onset to peak and expulsive phase and in-phase volume such as the duration of the glottic closure as explained in greater detail below. It is also possible to measure in-phase peak flow and the expulsive phase peak flow using such device.

FIGS. 23 and 24 show an embodiment of the nebulizer such as shown in FIG. 9 at 204 in which the air flow sensor that is associated with the main body 200 and configured to measure the air flow created by the patient's one of at least inhaling and exhaling air is formed as a separate flow meter device illustrated generally at 450 and which is removably attached to the main body and configured for use by a patient after nebulizing. For example, the nebulizer as shown in FIGS. 2-19 could have the separate flow meter device 450 attached by snap-on clips 452 or other means as shown in the example of FIG. 23. This flow meter device 450 can be readily attached and detached from the nebulizer. In one non-limiting example, the patient attaches the flow meter onto the nebulizer after initially using the nebulizer for nebulizing the mediation for intake. In another example, this flow meter device 450 could be integrally formed with the nebulizer at the back of its main body. As illustrated, the flow meter device has a similar configuration and dimension as the main body except it is slightly shorter and includes snap-on clips 452 to allow it to be snapped on and off. The device includes a flexible tube 456 with a mouthpiece 458. The expiratory channel valve 460 and intake channel valve 462 are shown at the side and the antenna 464 that could be a conformal antenna as partially shown. Although snap-on clips are illustrated, other attachment and fastening mechanisms could be used such as a tongue and groove attachment mechanism or a slide mechanism in which the separate flow meter device 450 slides onto the back of the main body of the nebulizer.

FIG. 24 is a block diagram showing basic components of the separate flow meter device 450 that is attached onto the main body using the clips 452 or other attachment mechanism. As illustrated, the device includes a processor 470 that is connected to a wireless module 472 that includes a wireless transceiver 473 in this example that sends data as wireless communications signals to the handheld processing device 560 such as shown in FIG. 25 and explained above for measuring and processing the various respiratory functions and processing the associated data, including air flow, air pressure, air resistance, Pulmonary Function Testing (PFT) results for respired air and data including results from voluntary cough testing (VCT) and involuntary reflex cough testing (iRCT). The antenna 464 as illustrated could be a conformal antenna. The flexible tube 456 with the mouthpiece 458 is shown and is attached to the flow meter 450. One or more valves are positioned in one or more air channels as part of the flow meter and connected to the flexible tube. In one example as illustrated, a central control valve 474 controls overall flow to and from inspiratory and expiratory channels 476,478 providing overall control of intake and exhaust of respired air as illustrated. This valve in this example is controlled by the processor. It can operate similar to the valve 290 for pulmonary testing and exercise. Air flow sensors 480 can be positioned in various channels for measuring flow, pressure and velocity of air while allowing the device to perform pulmonary function testing. An air flow sensor 480 could be located in the single inhale and exhale channel 482 connecting to the flexible tube or in the other inspiratory or expiratory air flow channels 476, 478. Different valves 460, 462 can be used as known to those in the art and the device is not limited to any one type. The device can operate as a differential pressure transducer in a non-limiting example and measure voluntary cough or reflex cough.

The flexible tube 456 could be removably attached to the body 484 of the flow meter device 450 in another example through an appropriate tube fitting 486 that allows the tube to be readily attached or removed as necessary. In operation, a patient could self-medicate using the nebulizer, turn the nebulizer function off and snap-on the flow meter (or flexible tube or other breathing tube if the flow meter is built-in) or already attached to the main body. The flow meter device sends test result data via the wireless module 472 and the flow and volume of air is measured and transmitted by the processor such as the handheld device 560. The processor 470 can also process data for respiratory function depending on the type of processor and programming. The data from the processing can be displayed on the display 490, which can display data about air resistance and pulmonary function and exercise in an example. Different air flow sensors can be used such as described above and the device is not limited to any one sensor. Also, a contact 491 can receive electrical signals from any sensor 280 such as shown in FIG. 20 if there is another contact on the nebulizer body and transmit them to the processor 470.

A patient (or clinician or physician) can perform a medical treatment with the nebulizer. It is then possible to operate the flow meter after nebulization to determine if the patient has improved due to the use and administration of the drug such as the tartaric acid. It is possible to measure and graph results through an air flow sensor as part of the flow meter device and transfer data to the handheld device (or other processing device) and measure flow and pressure over time. The adjustment 492 can be used to adjust air flow for spirometry such that the processor adjusts the valve 474 or other valves in this example. It is possible to adjust valves 460 and 462 to vary the resistance such that the intake and/or expiratory pressure is varied.

FIG. 25 is an illustration of an exemplary handheld processing device 560. More particularly, it should be understood that this handheld processing device 560 can be used by a nurse practitioner or doctor and receive input as wireless signals for flow meter testing as described above. Also, this handheld processing device 560 can incorporate the circuit and functions as disclosed in the copending and commonly assigned '316, '134, '125 and '251 applications that are incorporated by reference in their entirety and identified above. Catheters and other inputs can be connected to this handheld processing device 560 as explained in the above-identified and incorporated by reference patent applications.

FIG. 26 is a block diagram that illustrates a computer system 500 for the handheld processing device 560. Computer system 500 includes a bus 502 or other communication mechanism for communicating information, and a processor 504 coupled with bus 502 for processing information. Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Computer system 500 further includes a read only memory (ROM) 508 or other static storage device coupled to bus 502 for storing static information and instructions for processor 504.

Computer system 500 may be coupled via bus 502 to a display 512, such as a LCD, or TFT matrix, for displaying information to a computer user. An input device 514, for example buttons and/or keyboard, is coupled to bus 502 for communicating information and command selections to processor 504. Another type of user input device is cursor control, such as a mouse, a trackball, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane.

Computer system 500 operates in response to processor 504 executing one or more sequences of instruction. Execution of the sequences of instructions causes processor 504 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 504 for execution. Such a medium may take many forms, including but not limited to, non-volatile media, volatile media, and transmission media. Non-volatile media includes, for example, optical or magnetic disks. Volatile media includes dynamic memory, such as main memory 506. Transmission media includes coaxial cables, copper wire and fiber optics, including the wires that comprise bus 502. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 504 for execution. For example, the instructions may initially be carried on a magnetic disk of a remote computer. The remote computer can load the instructions into its dynamic memory and send the instructions over a telephone line using a modem. A modem local to computer system 500 can receive the data on the telephone line and use an infrared transmitter to convert the data to an infrared signal. An infrared detector can receive the data carried in the infrared signal and appropriate circuitry can place the data on bus 502. Bus 502 carries the data to main memory 506, from which processor 504 retrieves and executes the instructions. The instructions received by main memory 506 may optionally be stored on storage device 510 either before or after execution by processor 504.

The handheld device 560 preferably uses wireless technology that could include infrared (IR), Bluetooth, or RFID technology for communicating with the wireless transceiver in the wireless module of the flow meter or part of the nebulizer. The handheld processing device 560 includes a wireless module 580 that works in conjunction with the pressure transducer interface and controller 518 and the respiratory air flow sensor (flow meter) interface 581 and sends and receives readings through the antenna 582 or other system that could be used. The wireless module 580 could be located at different locations.

There now follows a general description of physiology for the involuntary reflex cough test (iRCT), which activates the Nucleus Ambiguus. The nebulizer with the flow sensing function is adapted for measuring both voluntary cough and involuntary reflex cough, such as explained in the incorporated by reference patent applications. The iRCT selectively activates the Medial Motor Cell Column (MMCC) of the spinal cord rather than the (Lateral) LMCC to fire muscles embryologically predetermined to be involuntary cough activated muscles in the pelvis. In the past, urologists did not selectively activate MMCC without overtly activating the LMCC. Magnetic stimulation or electrical spinal cord stimulation activate both cell columns and thus it is not possible to sort out pathology with these. Magnetic stimulation or other approaches from CNS activation set off both columns.

The pelvic muscles that typically are activated with MMCC cough activation include the lumbar-sacral L5/S1 paraspinal axial musculature, which facilitates inpatient continence screening. An example is through MMCC iRCT muscle activation, obtaining L5/S1 paraspinal firing but not L5/S1 lateral gastrocnemius activation because the gastroc muscles are limb muscles activated primarily through the LMCC.

The L-S paraspinals are easier to access with a large pad placed above the sacrum on the midline that contains active, reference and ground combined. It is not important to determine lateralization of the activity like needle EMG for radiculopathy, but only if activation occurs reflexively where the onset latency is under the pressure activation of the abdomen such as the Levator Ani. This is a poor muscle for these purposes because people train it to activate and set their pelvis if the person senses any intra-abdominal pressure elevation. Also, it is difficult to get pads to stick to that area with hair, perspiration, fungal infections or bowel/bladder incontinence present, and other factors.

Some examples have been developed and studied, including a normal CNS patient with Lumax bladder and bowel catheters and pads at L5/S1 paraspinals and a separate EMG machine and electrodes at the pelvic floor in a standard 3:00 and 9:00 o'clock set-up to demonstrate simultaneous involuntary activation with iRCT. This sets off the pelvic floor muscles. Thus, normal airway protection data is obtained and normal CNS data to L1 (where spinal cord ends). The set-up includes a complete T12 that cannot void and needs intermittent catheterization with the same set up, thus demonstrating data for normal airway but no L5/S1 EMG activation by MMCC with all the other data necessary to prove an unsafe bladder by the algorithm. A quadriplegic can demonstrate abnormal airway protection and abnormal EMG activation at both paraspinal and pelvic floor muscles with unsafe bladder measurements that follow the algorithm.

It should be understood that iRCT is an involuntary maneuver that activates embryologically predetermined muscles for airway protection and continence that travel primarily through the MMCC in the spinal cord. Different varieties of lesions are captured and determined with summated interval data approach for general screening purposes.

It is known that the laryngeal cough reflex (LCR) is a strong brainstem-mediated reflex that protects the upper airway by preventing aspiration, or the entrance of secretions, food, and/or fluid into the airway below the level of the true vocal cords (rima glottidis), through elicitation of an involuntary cough. The LCR is activated through the stimulation of cough receptors in the vestibule of the larynx. One way this is achieved is through the inhalation of chemostimulants, such as tartaric acid. Studies have shown that if the LCR is intact, the subject will involuntarily cough (normal LCR) upon inhaling a solution containing TA.

In one non-limiting example, the iRCT involves the inhalation of a nebulized 20% normal saline solution of L-TA (Tartaric Acid). Subjects are asked to perform 1 to 3 effective, full inhalations (about 15-20 second exposure by mouth for tidal breathing wearing a nose clip) from a standard jet nebulizer with at least 50 psi from an oxygen wall unit or tank that produces an average droplet diameter of 1 to 2 microns or less. The nebulizer output is 0.58 mL/min. The initiation of an involuntary cough reflex after any one of the inhalations is the end point of the procedure.

Nebulized TA is a chemical tussive that stimulates irritant receptors in the mucosa of the laryngeal aditus. Mild irritation of these receptors results in nerve impulses being conveyed by the internal branch of the superior laryngeal nerve (ibSLN) to bulbar centers of the brainstem. This nerve constitutes the afferent sensory component of the LCR arc. The efferent component of the LCR is mediated through the vagus, phrenic, intercostals and thoracoabdominal nerves.

Inhaled TA is selective in stimulating rapidly adapting ("irritant") receptors (RARs), in the supraglottic region. In humans, bilateral anesthesia of the ibSLN abolishes TA-induced cough and permits tidal breathing of the nebulized vapor without coughing, supporting the idea that the RARs are responsible for TA-induced cough.

The physiological response from inhalation of TA in a normal subject is abrupt, forceful coughing of short duration. Using a 20% solution of inhaled nebulized TA is a safe, reliable way to assess the sensation in the supraglottic laryngeal region and subsequently the neurologic circuitry of the LCR. In addition, the ability of the iRCT to predict the integrity of the protective LCR in subjects with stroke has been studied.

A 20% solution of TA as an aerosol causes cough by stimulating sensory nerves in and under the laryngeal epithelium. These nerves have been identified histologically, and the reflexes they cause have been identified. The sensory nerves can be stimulated by both non-isosmolar and acid solutions. Tartaric acid may act in both ways, but the balance between them is uncertain.

The nerves are stimulated by the opening of membrane channels in the nerve terminals. More than 20 categories of channels have now been identified, the opening of which will allow calcium flow into the nerve (and also sodium, with exit of potassium), with the result that an action potential is set up, which travels to the brainstem in the central nervous system (CNS), and reflexively induces cough.

Several different types of sensory nerve ending in the larynx have been identified that may mediate cough and other defensive reflexes. They have been extensively studied, mainly in experimental animals by recording the action potentials in their nerve fibers. The probable candidates for cough are the RARs or 'irritant' receptors. These are highly sensitive to mechanical stimuli, to hyperosmolar solutions, and to acids.

Once stimulated, the sensory nerves will induce a variety of defensive reflexes, which protect the lungs from invasion of harmful material. These include cough (an inspiration, followed by a forced expiration against a closed glottis, followed by opening of the glottis with an expiratory blast); the laryngeal cough expiratory reflex (LCER, a powerful expiratory effort with the glottis open); and the glottal closure reflex. In some instances a reflex apnea can be produced. The balance of these reflexes may depend on the nature and the strength of the stimulus. In the case of TA, the LCER seems to be dominant, possibly followed by glottal closure, and the pathophysiological advantage of this response in preventing aspiration is obvious.

There now follows an analysis and test results in greater detail that explain the advantageous use of the involuntary reflex cough test (iRCT) for investigating and diagnosing not only SUI, but also physiological abnormalities such as neurologic deficiencies. The nebulizer as described can be used in conjunction with testing. It should be understood that there are differences between normal and neurological patients.

The EMG from the parineal muscles respond almost simultaneously to the onset of the voluntary cough because the patient does not want to leak. With the involuntary reflex cough test, on the other hand, the fast fibers that are set off reach the abdominal muscles quickly, such as in 17 milliseconds as an example, the patient is not able to set their pelvis. In some of the graphs reflecting urodynamic testing as will be described, it is evident that the onset of the EMG activity does not happen at the same time the pressure rises. Some people that have neuropathy, for example, spinal stenosis or nerve injury (even if it is mild), have a situation that prevents the reflexes from closing before the pressure has changed to push on the bladder. It is not possible to obtain this diagnostic tool methodology unless the involuntary cough reflex test is accomplished. When the involuntary reflex cough test is accomplished, it is possible to demonstrate a latency delay and show that the pathophysiology is a neuropathic problem rather than a structural problem. It is possible to separate the pathophysiology using the involuntary reflex cough test and methodology as described.

In one example, a female patient could have a weak spinal cord and her physiology is normal. This patient may not leak during the test, but the patient cannot protect her airway. Thus, using the methodology apparatus and system associated with the involuntary reflex cough test, in accordance with non-limiting examples, it is possible not only to diagnose an unprotected airway, but also to diagnose normal bladder physiology, including the neurophysiology to the patient's sphincter closure process. This is advantageous because it is then possible to determine when someone cannot protect their airway, even though they may have a normal bladder. Conversely, there are patients with a normal airway, but cannot control their bladder. This process and system as described is able to make that diagnosis and thus the involuntary reflex cough test is an advantageous medical diagnostic tool. For example, it is possible to have a patient with a poorly functioning bladder and normal airway and use of the test allows a doctor to find lower urinary tract symptoms and neuropathology. It becomes possible to diagnose a level of lesion in a patient with a full comprehensive neurologic examination using the involuntary reflex cough test, methodology and apparatus as described.

As will be described in detail later, the various components such as the nebulizer, one or more catheters, any pads for the paraspinal muscles when EMG is used, and drug as part of the nebulizer are inserted in a kit for use at the clinic, hospital or setting. Those components can be discarded after use. The handheld device, of course, will be used again. Use of the kit provides a clinician, doctor or other medical professional the readily available diagnostic tool to determine if a patient has a questionable airway and determine bladder physiology at the same time, all with the use of the one kit.

A kit that is marketed for the iRCT diagnostic tool could include the nebulizer and its drug as TA in one example and one or more pads for the electrodes at the paraspinal and use with EMG. The pad may only be necessary for stress incontinence determinations. A catheter is included in another kit example for use in measuring airway and intra-abdominal pressure. In one non-limiting example, a pad can be placed on a catheter to determine urine leakage and aid in determining stress incontinence. Pressure data is sent to the handheld device in some examples. Obtaining any EMG values from the paraspinal in conjunction with the urology analysis is advantageous. It is possible in one example to measure pressure from a bladder catheter and determine at the same time EMG signals using the EMG electrodes at the L5/S1 in conjunction with the measured involuntary reflex cough test and urology catheter sensing. This is advantageous compared to placing electrodes at the perineal muscles on each side of the sphincter.

It has been found that EMG signals obtained from the perineal muscles have EMG activity from the non-involuntary muscles, i.e., the voluntary muscles blacking out and making analysis difficult because of the signal interference. When the electrodes are placed at the back at the L5/S1 junction, on the other hand, there is nothing else but the paraspinal muscles. It is bone below on each side at the L5/S1 junction. The electrical impulses can be obtained that determine the number of cough impulses coming down through the patient. This is accomplished even if a person has much adipose. The electrode pad used at the L5/S1 junction, in one non-limiting example, typically has an active reference and ground. A pad holds this active reference and ground and the leads as the active reference and ground are plugged into the handheld device (or wireless sensing device in another example) and transmit data to the processor. At least one catheter is also plugged into the handheld device (or wireless sensing device) and measures bladder pressures. A rectal catheter can also be used in some examples. The processor receives EMG signals and determines when the cough event is over.

The involuntary coughs are not hidden by interference when measured from the lower back at the paraspinals as described. This allows a clinician to determine coughs from the bladder when the EMG located at the L5/S1. In one aspect, the area under curve and the average pressure is determined for the cough event corresponding to the involuntary reflex cough test. When this involuntary component of the cough ends, in one example, it becomes silent EMG activity for a period of time. The pressures are at baseline for a period of time, which corresponds in one example to an inhalation. The involuntary component is over.

Sometimes with the involuntary reflex cough test, the cough occurs six times without breathing, but when the patient stops to breathe, the event is over. Using the programming applied with the processor in the handheld device, it is possible to calculate the variables inside the wave as to the involuntary cough and determine airway protection capability. Thus, it is possible to determine and measure cough by defining through appropriate data processing the involuntary cough event compared to the whole cough epoch. For example, a patient could cough ten times, but only the first four are part of the involuntary cough event. The coughs after that event are not part of the epoch.

The programming includes algorithm branches resulting in a conclusion of unsafe bladder based on the data analysis. It is possible to calculate from the waveforms information necessary for assessing airway protection ability. It should be understood that taking the EMG from the L5/S1 is also a better situation for the doctor or clinician, and the patient, since it is more acceptable in a hospital, outpatient or inpatient setting. The doctor or clinician does not have to bend down or stoop and look near the crotch area and place pads since the EMG can now be taken from the paraspinals. Also, the placement of pads and electrodes at the paraspinals is advantageous when patients are standing. If pads are placed at the perineal area, sweat and other problems could cause those pads to become loose and good signals may not be obtained. Also, it should be understood that the perineal muscles do not fire involuntarily. The sphincter may fire involuntarily, but that would create more noise as noted before. Electrodes are not placed at the vagina, but are placed at the paraspinal area instead.

This information obtained from iRct and the EMG taken at the paraspinals allows the doctor or clinician to obtain data leading directly to a diagnosis. For example, some patients that have urinary stress incontinence may have a normal airway in this analysis. It has been found by experimentation that the normal airway is about 50 centimeters water average intra-abdominal pressure. It should be understood that the vesicular pressure (bladder pressure) can track intra-abdominal pressure and terms are often similar and used together. "Bladder" or intravesicular pressure is often used to determine and equate with intra-abdominal pressure. The two are sometimes used interchangeably. Stress urinary incontinence and/or bladder physiology can be diagnosed. The system and method as described leads directly to diagnosis. Fifty centimeters average intra-abdominal pressure over time has been found to correspond to an involuntary reflex cough test normal airway. Thus, the standard deviations or other percentages from that value are used in one non-limiting example to determine an abnormal airway. In a conducted study, the actual value is determined to be about 50.6 centimeters water as compared to voluntary cough values of about 48 centimeters of water. In an outpatient setting, it is possible to have the nebulizer (and drug) and only a pad and test SUI. In hospitalized patients or inpatient settings, this combination is used to measure airway and bladder physiology and the test combination includes a catheter.

It should be understood that the involuntary cough reflex test (iRCT) gives a higher pressure average than obtained using a voluntary cough test. The involuntary cough reflex test is thus a valuable medical diagnostic tool. In one example, four variables are significant in this analysis. These variables include: (1) duration of the event; (2) average intra-abdominal pressure of the event; (3) peak intra-abdominal pressure (max) of the event; and (4) area under the curve. Using these four variables, it is possible to process the received data and obtain a specific diagnosis that could not otherwise be obtained without the use of the involuntary reflex cough test. Individual deficits in a specific variable or combination of variables are used to characterize specific diseases and problems and useful as a medical diagnostic tool.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed:

1. A nebulizer that provides air flow measurement, comprising:
   a main body configured to be grasped by a user and comprising an air channel section and further comprising a mixing chamber and a venturi positioned to be placed within the patient's oral cavity and configured to receive medicine and air and mix the medicine and air within the mixing chamber and receive the air flow through the venturi and cause the medicine entering the mixing chamber to be atomized by the action of air flowing through the venturi during nebulization; and
   a mouthpiece separate from the venturi and an air flow sensor operatively connected thereto and configured to measure the air flow created by the patient's one of at least inhaling and exhaling air through the mouthpiece as the main body is grasped by a user.

2. The nebulizer according to claim 1, and further comprising a processor associated with the air flow sensor and configured to process the measured air flow over time to determine a respiratory function of the patient.

3. The nebulizer according to claim 2, wherein said processor is configured to process measured air flow over time to determine a neurological deficiency in a patient based on air flow measurements derived from an involuntary reflex cough.

4. The nebulizer according to claim 2, and further comprising a wireless module connected to the processor and configured to transmit wireless signals containing data about the measured air flow created by the patient's one of at least inhaling and exhaling air.

5. The nebulizer according to claim 1, and further comprising an air flow metering valve connected to the mouthpiece and configured to adjust the resistance to air flow through the mouthpiece to a predetermined level for respiratory exercise training and incentive spirometry use.

6. The nebulizer according to claim 1, wherein said mixing chamber in said main body is configured as a rainfall chamber and a diffuser is positioned within the rainfall chamber upon which the medicine that is nebulized impacts and configured to break up droplets of medicine expelled from the venturi into smaller sizes.

7. The nebulizer according to claim 1, and further comprising a plurality of medicine receivers carried by the main body, each shaped to match a shape uniquely associated with a different medicine receiver, and said air channel section is configured to receive medicine from a medicine container that is received within the medicine receiver.

8. The nebulizer according to claim 1, and further comprising air curtain conduits that are configured to supply a curtain of air above and below the nebulized medicine and air to enhance penetration of nebulized medicine into the airway of the patient.

9. The nebulizer according to claim 1, wherein said air flow sensor is configured to measure air velocity.

10. The nebulizer according to claim 1, wherein said air flow sensor is configured to measure air pressure.

* * * * *